(12) United States Patent
Stahl et al.

(10) Patent No.: US 7,951,912 B2
(45) Date of Patent: May 31, 2011

(54) POLY-β-PEPTIDES FROM FUNCTIONALIZED β-LACTAM MONOMERS AND ANTIBACTERIAL COMPOSITIONS CONTAINING SAME

(75) Inventors: Shannon S. Stahl, Madison, WI (US); Samuel H. Gellman, Madison, WI (US); Sarah Lee, Buffalo Grove, IL (US); Mehmet F. Ilker, Madison, WI (US); Bernard Weisblum, Madison, WI (US); Denis Kissounko, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 358 days.

(21) Appl. No.: 11/510,017

(22) Filed: Aug. 25, 2006
(Under 37 CFR 1.47)

(65) Prior Publication Data
US 2007/0087404 A1   Apr. 19, 2007

Related U.S. Application Data

(60) Provisional application No. 60/712,214, filed on Aug. 29, 2005, provisional application No. 60/711,977, filed on Aug. 26, 2005.

(51) Int. Cl.
*C12P 21/06* (2006.01)
*C07K 1/02* (2006.01)

(52) U.S. Cl. ...................................... 530/333; 435/68.1

(58) Field of Classification Search ........................ None
See application file for complete search history.

(56) References Cited

U.S. PATENT DOCUMENTS

| | | |
|---|---|---|
| 3,583,947 A | 6/1971 | Schmidt et al. |
| 4,677,189 A | 6/1987 | Mottus et al. |
| 4,695,611 A | 9/1987 | Mottus et al. |
| 5,756,647 A | 5/1998 | Schmid et al. |
| 5,864,007 A | 1/1999 | Schmid et al. |
| 6,013,758 A | 1/2000 | Schmid et al. |
| 6,060,585 A | 5/2000 | Gellman et al. |
| 6,613,876 B1 | 9/2003 | Gellman et al. |
| 6,617,425 B1 | 9/2003 | Seebach et al. |
| 6,683,154 B1 | 1/2004 | Gellman et al. |
| 6,818,732 B2 | 11/2004 | Deming et al. |
| 6,835,774 B2 | 12/2004 | White et al. |
| 6,881,819 B2 | 4/2005 | Schmid et al. |
| 2003/0083460 A1* | 5/2003 | Deming et al. ............... 528/328 |

FOREIGN PATENT DOCUMENTS

WO   WO 03/008439 A1   1/2003

OTHER PUBLICATIONS

Durham TB, Miller MJ, An Enantioselective Synthesis of Differentially Protected Erythro-a,b-Diamino Acids and Its Application and Its Application to the Synthesis of an Analogue of Rhodopeptin B5, Journal of Organic Chemistry, 2003, 68: 35-42.*

Chiba H, Agematu H, Sakai K, Dobashi K, Yoshioka T, Rhodopeptins, Novel Cyclic Tetrapeptides with Antifungal Activities from Rhodococcus sp. III. SYnthetic Study of Rhodopeptins, Journal of Antibiotics, 1999, 52(8): 710-720, abstract only enclosed.*

Appella et al. (1996) β-Peptide Foldamers: Robust Helix Formation in a New Family of β-Amino Acid Oligomers, *J. Am. Chem.*, 118:13071-13072.

Cheng et al. (2001) Controlled Polymerization of β-Lactams Using Metal—Amido Complexes: Synthesis of Block Copoly(β-peptides), *J. Am. Chem. Soc.* 123:9457.

Cheng, Gellman & Degrado, (2001) β-Peptides: From Structure to Function, *Chem. Rev.* 101:3219-3932.

Dener et al. (2001) Large-Scale Synthesis of FMOC-Protected Non-Proteogenic Amino Acids: Useful Building Blocks for Combinatorial Libraries, *Organic Process Research and Development* 5:445-449.

Gellman et al. (1998) Foldamers: A Manifesto, *Acc. Chem. Res.* 31:173-180.

Peelen et al. (2004) Synthesis of 4,4-Disubstituted a-Aminocyclopentanecarboxylic Acid Derivatives and Their Incorporation into 12-Helical β-Peptides, *Organic Letters* 6(24):4411-14.

Graf et al. (1962) β-Lactams, Their Polymerization and Use as Raw Materials for Fibers, *Angew. Chem. Int. Ed.* 1:48/4881.

Hamuro et al. (1999) De Novo Design of Antibacterial β-Peptides, *J. Am. Chem. Soc.* 121:12200-12201.

Hashimoto et al. (2000) *Prog. Polym. Sci.* 25: 1411-1462.

Huang et al. (1984) A Convenient Method for the Construction of β-Lactam Compounds from β-Amino Acids Using 2-chloro-1-Methyl Pyridinium Iodide as Condensing Reagent, *Chem. Lett.* 1465-1466.

Lopez-Carrasquero et al. (1994) Poly(α-n-alkyl-L-aspartate)s: a new family of helical nylons, *Polymer* 35:4502-4510.

Park et al. (1996) Preparation of Phenolic Paclitaxel Metabolites, *J. Med. Chem.*, 39:2705-2709.

Parsons et al. (1996) Tandem Reactions of Anions: A Short and Efficient Route to ± Anatoxin-α, *Tetrahederon*, 52:11637-11642.

Sebenda et al. (1976) Preparation and Heat of Polymerization of 3-Methyl-3-Butyl-2-Asetidinone, *J. Polym. Sci: Pol. Chem.* 14:2357-2363.

Seebach et al. (1996) β-Peptides: Synthesis by *Arndt-Eistert* Homologation with Concomitant Peptide Coupling. Structure Determination by NMR and CD Spectroscopy and by X-Ray Crystallography. Helical Secondary Structure of β-Hexapeptide in Solution and Its Stability towards Pepsin, *Helv. Chim. Acta.* 79:913-914.

Seebach et al. (1996) Probing the Helical Secondary Structure of Short-Chain β-Chain β-Peptides, *Helv. Chim. Acta.* 79:2043-2066.

* cited by examiner

*Primary Examiner* — Julie Ha

(74) *Attorney, Agent, or Firm* — Joseph T. Leone, Esq.; DeWitt Ross & Stevens S.C.

(57) ABSTRACT

Disclosed is a method of making β-polypeptides. The method includes polymerizing β-lactam-containing monomers in the presence of a base initiator and a co-initiator which is not a metal-containing molecule to yield the product β-polypeptides. Specifically disclosed are methods wherein the base initiator is potassium t-butoxide, lithium bis(trimethylsilyl) amide (LiN(TMS)$_2$), potassium bis(trimethyl-silyl)amide, and sodium ethoxide, and the reaction is carried out in a solvent such as chloroform, dichloromethane, dimethylsulfoxide, or tetrahydrofuran.

12 Claims, 4 Drawing Sheets

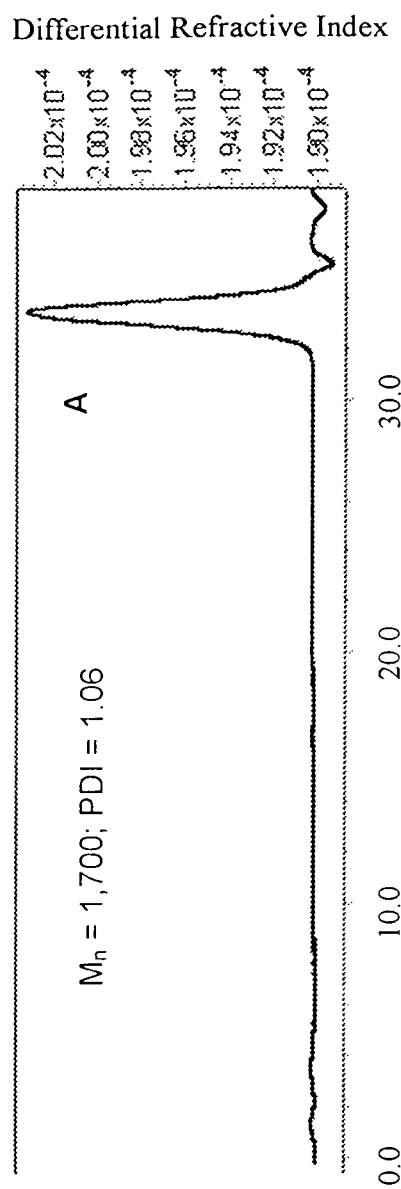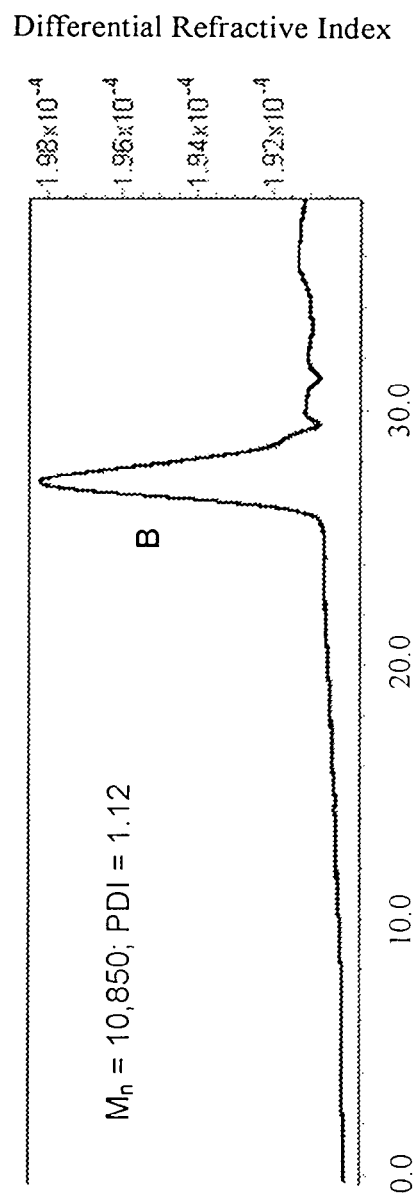

POLY-β-PEPTIDES FROM FUNCTIONALIZED β-LACTAM MONOMERS AND ANTIBACTERIAL COMPOSITIONS CONTAINING SAME

CROSS-REFERENCE TO RELATED APPLICATIONS

Priority is hereby claimed to provisional application Ser. No. 60/712,214, filed 29 Aug. 2005, and provisional application Ser. No. 60/711,977, filed 26 Aug. 2005, both of which are incorporated herein.

FEDERAL FUNDING STATEMENT

This invention was made with United States government support awarded by the following agency: NSF 0425880. The United States has certain rights in this invention.

BACKGROUND

In recent years, a number of academic research groups have directed their interests toward oligomers and polymers comprised of β-amino acid residues. These compounds are collectively referred to herein as β-peptides or β-polypeptides. β-polypeptides differ from naturally occurring α-polypeptides by the presence of an additional carbon atom (the β-carbon) situated between the amino terminus and the carboxy terminus in the backbone of the polypeptide.

Over the past decade, the synthesis, properties and functions of β-peptides have been the subject of extensive study by a number of research groups. See, for example, Cheng, Gellman & DeGrado (2001) Chem. Rev. 101:3219-3232. The interest in β-polypeptides is due, in part, to the discovery that these compounds can adopt stable secondary structures ("foldamers") that mimic natural peptides. See Gellman et al. (1998) Acc. Chem. Res. 31:173. Certain β-polypeptides have been shown to exhibit important biological activity, including cholesterol absorption inhibition and antimicrobial activity. Oligo-β-peptides generally must be prepared via solid-phase synthesis, a relatively costly and labor-intensive technique that restricts the scope and scale of possible uses for β-polypeptides, despite their favorable activities.

β-peptides are entirely non-natural. Thus, β-peptides are resistant to enzymatic degradation, in contrast to α-peptides. In short, β-peptides mimic α-peptides in many key aspects (most notably the adoption of stable secondary conformation) but because they are non-natural, β-peptides are not as prone to breakdown in biological milieus as are naturally occurring α-peptides.

Large-scale synthesis of β-peptides is difficult because the standard preparative methods involve step-wise, residue-by-residue synthesis. Thus, much of the scientific literature relating to β-polypeptides approaches the subject as a direct spin-off from α-polypeptide chemistry: The β-polypeptides are synthesized by solution-phase or solid-phase chemistries, residue-by-residue. In the U.S. patent literature, see, for example, U.S. Pat. Nos. 6,060,585; 6,613,876; and 6,683,154, all to Gellman et al. See also U.S. Pat. No. 6,617,425, to Seebach. In the scientific literature, see, for example, Gellman et al. (2004) Organic Letters 6(24):4411-4; and Gellman et al. (1996) J. Am. Chem. Soc. 118:13071. See also Seebach et al. (1996) Helv. Chim. Acta. 79:913-941; and Seebach et al. (1996) Helv. Chim. Acta. 79:2043-2066. Antibacterial compositions containing β-peptides are described in Hamuro et al. (1999) J. Am. Chem. Soc. 121:12200-12201.

Polymerization routes to β-peptides have been problematic mainly due to the poor solubility of the resulting β-polypeptide chain, which limits the ability of the conventional routes to yield large β-polypeptides having a diverse number of derivatives. One route that has been investigated by a number of groups is a ring-opening polymerization of β-lactams. See Graf et al. (1962) Angew. Chem. Int. Ed. 1:481; Sebenda et al. (1976) J Polym Sci: Pol. Chem. 14:2357; Lopez-Carrasquero et al. (1994) Polymer 35:4502; Garcia-Alvarez et al. (1994) Syn. Commun. 24:745; Hashimoto (2000) Prog. Polym. Sci. 25:1411; and Cheng et al. (2001) J. Am. Chem. Soc. 123:9457. Each of these routes, however, suffers from serious shortcomings related to low product solubility and difficulty in characterizing the resulting products. Despite their apparent convenience, the polymerization techniques described in these references require high-purity reagents and solvents. Reaction conditions must be carefully controlled and maintained or the polymerization falters. The conventional reactions as taught in the cited references simply are intolerant to impurities. The solvent systems that can be employed are also limited. Sebenda et al. frankly stated that "It is known that polymers of β-lactams are only soluble in strongly polar solvents which interfere with anionic polymerization." In other words, the solvents required to keep the growing polymer chain in solution are solvents that are not conducive to anionic polymerization.

The patent literature likewise contains a number of issued U.S. patents directed to various aspects of lactam polymerization. See, for example, Deming et al., U.S. Pat. No. 6,818,732. See also U.S. Pat. Nos. 6,881,819; 6,835,774; 6,013,758; 5,864,007, 5,756,647, 4,695,611; and 4,677,189.

Thus, there remains a long-felt and unmet need for a synthetic route to make large β-peptides (e.g., about 1 kDa or larger) that can be controlled to yield homopolymers, random co-polymers, block copolymers, etc. of a desired molecular weight range and distribution.

SUMMARY OF THE INVENTION

Thus, the invention is directed to a method of making β-polypeptides. The method comprising polymerizing β-lactam-containing monomers in an organic solvent in the presence of a base initiator and a co-initiator which is not a metal-containing molecule. It is generally preferred that the co-initiator is a compound of formula

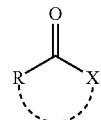

wherein X is independently a leaving group and R is independently a base-stable moiety, or R and X, together with the carbon atom to which they are attached, define a substituted or unsubstituted, five- to twelve-membered ring having an intramolecular leaving group. Preferably the ring is monocyclic. When R and X are combined, the resulting ring may be fully saturated, or may contain one or more unsaturations. The ring may also contain one or more heterocyclic atoms, generally selected from N, O and S. For example, the co-initiator can be a cyclic anhydride, such as succinic anhydride or maleic anhydride. The co-initiator can also be selected from the group consisting of:

wherein X is a leaving group selected from the group consisting of alkoxide, amidate, carboxylate, halide, imidazolate, lactamate, and thiolate; and R is a base-stable moiety selected from the group consisting of linear, branched, or cyclic alkyl, alkenyl, alkynyl, substituted or unsubstituted aryl, and substituted or unsubstituted arylalkyl, provided that the co-initiator is not an N-acyl-β-lactam.

In another version of the invention, at least one of the β-lactam-containing monomers comprises a fused bicyclic β-lactam moiety.

In yet another version of the invention, the method uses at least one β-lactam-containing monomer is selected from the group consisting of:

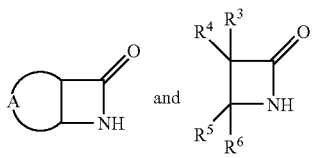

wherein A, together with the carbon atoms to which it is attached is selected from the group consisting of substituted or unsubstituted $C_5$-$C_{12}$ cycloalkyl, $C_5$-$C_{12}$ cycloalkenyl, and five- to twelve-membered heterocyclic; and $R^3$, $R^4$, $R^5$, and $R^6$ are each independently selected from the group consisting of hydrogen, substituted or unsubstituted $C_1$-$C_6$-alkyl, aryl, $C_1$-$C_6$-alklyaryl, amino, protected-amino, amino-$C_1$-$C_6$-alkyl, and protected-amino-$C_1$-$C_6$-alkyl. In a preferred route to yield β-polypeptides having an amino sidechain, at least one of $R^3$, $R^4$, $R^5$, or $R^6$ is selected from the group consisting of amino, protected amino, amino-$C_1$-$C_6$-alkyl and protected amino-$C_1$-$C_6$-alkyl.

The base initiator is generally selected from the group consisting of KOtBu, LiN(TMS)$_2$, KN(TMS)$_2$, NaOEt, Sc(N(TMS)$_2$)$_3$, Al$_2$(N(Me)$_2$)$_6$, Al(N(TMS)$_2$)$_3$, Zn(N(TMS)$_2$)$_2$, Sn(N(TMS)$_2$)$_2$, and CpTi(N(Me)$_2$)$_2$Cl. This list is non-limiting and other base initiators can be used.

The preferred solvents in which to carry out the method are chloroform, dichloromethane, dimethylsulfoxide, and tetrahydrofuran. Other suitable solvents and mixed solvent systems may also be used.

The polymerization may be carried out using at least two different β-lactam-containing monomers to yield a co-polymer (e.g., a random co-polymer or a block co-polymers)

In the preferred version, the polymerization reaction is carried out at a temperature≦about 50° C., preferably≦about 30° C.

Another version of the invention is directed to a method of making β-polypeptides comprising: polymerizing bicyclic, β-lactam-containing monomers in the presence of a base initiator and a co-initiator which is not a metal-containing molecule, wherein the bicyclic, β-lactam-containing monomers are selected from the group consisting of:

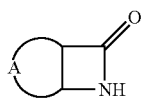

wherein A, together with the carbon atoms to which it is attached is selected from the group consisting of substituted or unsubstituted $C_5$-$C_{12}$ cycloalkyl, $C_5$-$C_{12}$ cycloalkenyl, and five- to twelve-membered heterocyclic. The co-initiators and other reaction conditions are as noted in the preceding paragraphs.

Another version of the invention is a method of making β-polypeptides comprising polymerizing β-lactam-containing monomers in the presence of a base initiator and a co-initiator which is not a metal-containing molecule, wherein the β-lactam-containing monomers include a monomer selected from the group consisting of:

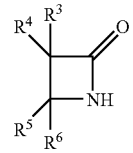

wherein $R^3$, $R^4$, $R^5$, and $R^6$ are each independently selected from the group consisting of hydrogen, substituted or unsubstituted $C_1$-$C_6$-alkyl, aryl, $C_1$-$C_6$-alklyaryl, amino, protected-amino, amino-$C_1$-$C_6$-alkyl, and protected-amino-$C_1$-$C_6$-alkyl; and wherein at least one of $R^3$, $R^4$, $R^5$, or $R^6$ is selected from the group consisting of amino, protected amino, amino-$C_1$-$C_6$-alky, 1 and protected amino-$C_1$-$C_6$-alkyl. This approach yields a β-polypeptide product having an amino side-chain.

Another version of the invention is directed to a method of making β-polypeptides comprising polymerizing monomers comprising substituted β-lactam-containing moieties, including at least one bicyclic β-lactam-containing monomer, in an organic solvent, in the presence of a base initiator and a co-initiator which is not a metal-containing molecule, at a temperature≦about 50° C., wherein:

the solvent is selected from the group consisting of chloroform, dichloromethane, dimethylsulfoxide, and tetrahydrofuran;

the base initiator is selected from the group consisting of KOtBu, LiN(TMS)$_2$, KN(TMS)$_2$, NaOEt, Sc(N(TMS)$_2$)$_3$, Al$_2$(N(Me)$_2$)$_6$, Al(N(TMS)$_2$)$_3$, Zn(N(TMS)$_2$)$_2$, Sn(N(TMS)$_2$)$_2$, and CpTi(N(Me)$_2$)$_2$Cl; and the co-initiator is selected from the group consisting of:

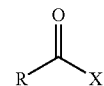

wherein X is a leaving group selected from the group consisting of alkoxide, amidate, carboxylate, halide, imidazolate, lactamate, and thiolate; and R is a base-stable moiety selected from the group consisting of linear, branched, or cyclic alkyl, alkenyl, alkynyl, substituted or unsubstituted aryl, and substituted or unsubstituted arylalkyl, and provided that the co-initiator is not an N-acyl-β-lactam.

Yet another version of the invention is directed to a method of making β-polypeptides comprising polymerizing monomers comprising substituted β-lactam-containing moieties, including at least one bicyclic β-lactam-containing monomer, in an organic solvent, in the presence of a base initiator and a co-initiator which is not a metal-containing molecule, at a temperature ≦ about 50° C., wherein:

the solvent is selected from the group consisting of chloroform, dichloromethane, dimethylsulfoxide, and tetrahydrofuran;

the base initiator is selected from the group consisting of KOtBu, LiN(TMS)$_2$, KN(TMS)$_2$, NaOEt, Sc(N(TMS)$_2$)$_3$, Al$_2$(N(Me)$_2$)$_6$, Al(N(TMS)$_2$)$_3$, Zn(N(TMS)$_2$)$_2$, Sn(N(TMS)$_2$)$_2$, and CpTi(N(Me)$_2$)$_2$Cl; and the co-initiator is selected from the group consisting of:

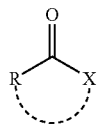

wherein X is independently a leaving group and R is independently a base-stable moiety, or R and X, together with the carbon atom to which they are attached, define a substituted or unsubstituted, five- to twelve-membered ring having an intramolecular leaving group.

A distinct advantage of the present invention is that it allows β-polypeptides of large molecular weight (up to about 20,000 Da) to be synthesized in large quantities, quickly, with great control over the polymerization conditions and the resulting product.

Another distinct advantage of the invention is that it allows for the preparation of β-polypeptides containing cationic side-chains or groups that can be converted into cationic side-chains after polymerization. For example, the inventive method can be used to make β-polypeptides having an amino moiety or a tBOC-protected amino moiety as a side-chain. These nitrogen-containing groups that can subsequently be manipulated (e.g. quaternized or otherwise further functionalized after polymerization).

BRIEF DESCRIPTION OF THE DRAWINGS

FIG. 4 is a gel permeation chromatography curve of a homopolymer made using compound 6.

FIG. 5 is a gel permeation chromatogram of degenerate block co-polymer made using compound 6.

DETAILED DESCRIPTION

Figure 1:
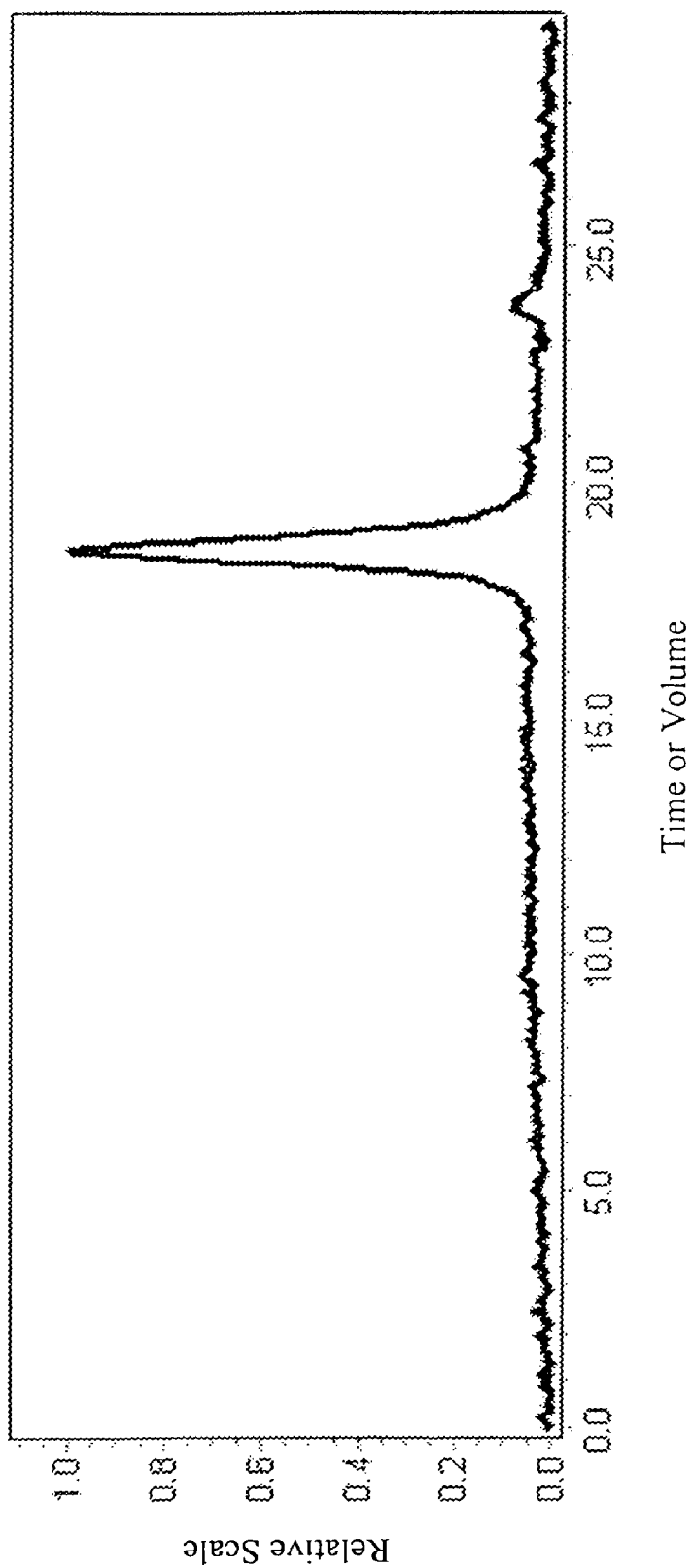
FIG. 1 is a gel permeation chromatography curve for the polymer formed from compound 3.

Abbreviations and Definitions:

The following abbreviations and definitions are used throughout the specification and claims. Terms not given an explicit definition here are to be given their art-accepted definition in the field of organic chemistry.

Amino=refers to a chemical group or moiety containing an sp$^2$ or sp$^3$ hybridized nitrogen atom, e.g., mono- and di-substituted amines where the nitrogen atom is in an sp$^3$ hybridization state, and pyridine and imidazole, where the nitrogen is in an sp2 hybridization state.

β-Lactam=azetidin-2-one:

β-Lactam-containing monomer=a polymerizable monomer that comprises a β-lactam moiety. β-lactam itself is a "β-lactam-containing monomer."

Et=ethyl.
GPC=gel permeation chromatography.
KN(TMS)$_2$=potassium bis(trimethylsilyl)amide.
KOtBu=potassium-tert-butoxide.
Lactamate=a moiety of the formula:

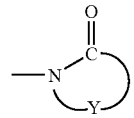

wherein Y is a substituted or unsubstituted C$_3$- to C$_{11}$-alkylene, alkenylene, or alkynylene. Y in combination with the nitrogen atom and the carbonyl carbon to which it is attached may define a monocyclic or bicyclic moiety. The monocyclic or bicyclic moiety may be unsubstituted or substituted with one or more of halo, alkyl, aryl (egg., phenyl), halo-substituted aryl, and/or alkyl-substituted aryl. The unqualified term "lactam" refers to the corresponding neutral molecule wherein the nitrogen atom is bonded to a hydrogen.

Leaving group=a labile atom or moiety that becomes detached from the co-initiator to yield a corresponding anion. As used herein, the term "leaving group" explicitly includes, without limitation, alkoxides, amidates, carboxylates, halides, imidazolates, lactamates, thiolates, and the like.

LiN(TMS)$_2$=lithium bis(trimethylsilyl)amide.
Me=methyl.
MeONa=sodium methoxide.
PDI=polydispersity index.
Phth=phthalimide.

Protecting Group/Protected Amine=A "protecting group" refers to a chemical moiety that exhibits the following characteristics: ) reacts selectively with the desired functionality in good yield (preferably at least 80%, more preferably at least 90%, more preferably at least 95%, still more preferably at least 99%) to give a protected substrate that is stable to the projected reactions for which protection is desired; 2) is selectively removable from the protected substrate to yield the desired functionality; and 3) is removable in good yield (preferably at least 80%, more preferably at least 90%, more preferably at least 95%, still more preferably at least 99%) by reagents compatible with the other functional group(s) present or generated in such projected reactions. Carbamate-, sulfonamide-, sulfamate-, and ammonium-forming protecting groups may all be used. Because the polymerization reaction occurs under basic conditions, base-stable protecting groups are preferred. The term "protecting group" explicitly includes, without limitation t-butoxycarbonyl (tBOC), benzyloxycarbonyl (Cbz), benzyl (Bn), and allyloxycarbonyl (alloc). A "protected amine" is an amine moiety protected by a "protecting group." A host of suitable amine-protecting groups are known in the art. See, for example, Greene & Wuts, "Protective Groups in Organic Synthesis, Third Edition," © 1999, Wiley-Interscience/John Wiley & Sons, New York, N.Y. (ISBN 0-471-16019-9).

Substituted or unsubstituted=when referring to a chemical moiety, the phrase "substituted or unsubstituted" means that the chemical moiety may appear as the basic unsubstituted moiety (e.g., an alkyl group having no other molecules beyond carbon and hydrogen), or the chemical moiety is substituted with one or more substituents, e.g. alkyl, halogen, alkoxy, acyloxy, amino, hydroxy, mercapto, carboxy, benzyl, etc.

TBBC=4-tert-butyl benzoyl chloride.

tBOC=tert-butoxycarbonyl.

Chemistry:

To overcome the limitations noted earlier, the present inventors have developed a synthetic route for fabricating β-peptides via a ring-opening polymerization of β-lactam-containing monomers. Exemplary reactions are shown in Reaction Schemes 1 and 2:

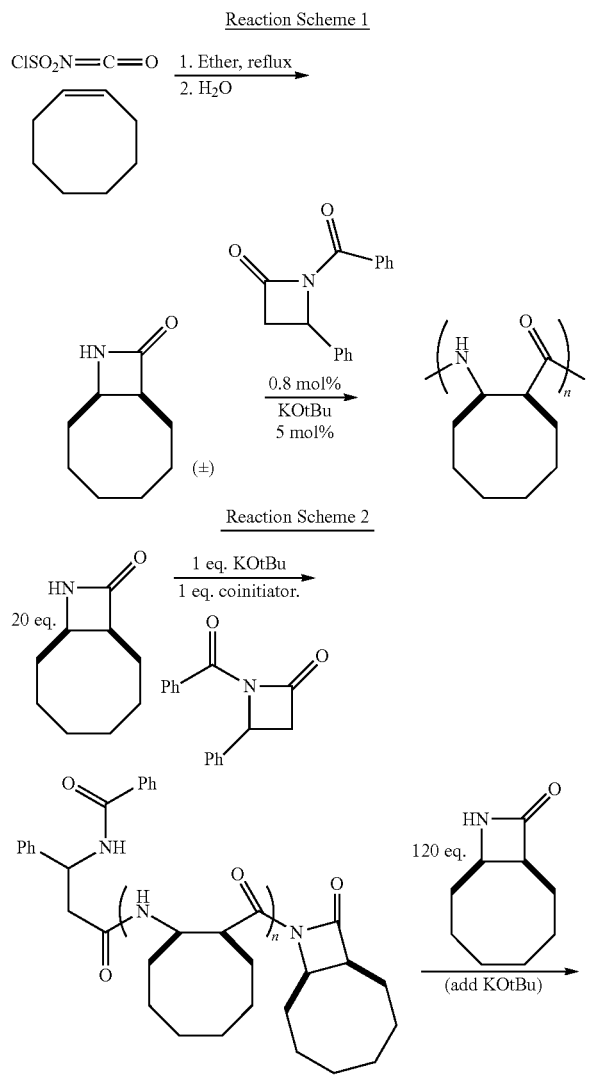

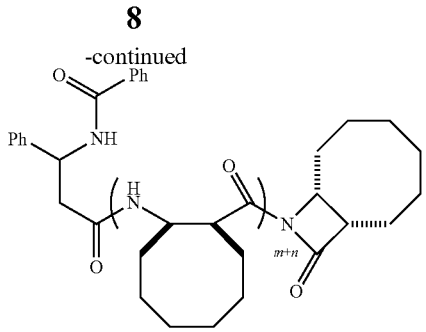

Note that the reactant monomers can be monocyclic (e.g., see monomers 10 and 13 in the Examples) or bicyclic (e.g., see Reaction Schemes 1 and 2, which illustrate the polymerization of compound 6; see the Examples). As shown in Reaction Schemes 1 and 2, the reaction proceeds in the presence of a base (potassium-t-butoxide in these two representative reactions) and a co-initiator (N-benzoyl-4-phenyl-β-lactam, also known systematically as N-benzoyl-4-phenyl azetidin-2-one).

The inventive reaction route is extremely versatile and has a great many benefits. Most notably, β-peptides of controlled molecular weights (Mn) of anywhere from about 1,000 Da to about 20,000 and larger can be obtained, using very common (and cheap) reagents. In typical reactions (where the time of reaction is not being unduly extended), β-peptides of controlled molecular weights of from about 1,000 Da to about 12,000 Da are readily obtained. Many of the β-polypeptide polymers thus obtained are soluble in common organic solvents, including dichloromethane, chloroform, and tetrahydrofuran (THF). The molecular weight distribution of the resulting polymers is quite narrow. For example, the monomer shown in Reaction Scheme 1 (a bicyclic compound comprising a β-lactam ring fused to a cyclooctane ring) was polymerized according to the present invention via an opening of the β-lactam ring to yield a polymer having an Mn of 11,400 Da (as measured by gel permeation chromatography; see FIG. 1), with a polydispersity index (PDI, calculated via gel permeation chromatography using a laser light-scattering detectors) of only 1.05. ("Polydispersity index" is also sometimes referred to as "molecular weight distribution" and is the ratio of the weight-average molecular weight (Mw) to number-average (Mn) molecular weight.) As a general rule, the inventive method will generate β-polypeptides with a PDI of less than about 2.0, more preferably less than about 1.5, and more preferably still less than about 1.3.

The reaction can proceed either in the presence or absence of a co-initiator. The polymerization reaction will proceed without an co-initiator, but the PDI tends to rise without the co-initiator. Suitable non-p-lactam co-initiators include aromatic acyl halides, preferably substituted or unsubstituted benzoyl halides, such as 4-tert-butyl-benzoyl chloride and 4-chloromethyl benzoyl chloride (both of which can be obtained commercially from several international suppliers, including Sigma-Aldrich, Milwaukee, Wis.), and the like.

As shown in Reaction Scheme 2, the reaction is a living polymerization and thus can be used to fabricate homopolymers, random co-polymers, block co-polymers, and the like. As used herein, the term "living polymerization" assumes its conventional meaning in the art, namely: a polymerization in which the ability of a growing polymer chain to terminate has been inhibited or abolished. Thus, the polymerization reaction can be carried out in stages, using monomers, first-stage pre-polymers, and/or second-stage (and/or subsequent-stage) pre-polymers as the reactants. Because the reaction is a living polymerization, the inventive route described herein provides exquisite control of the polymerization process.

Figure 2:
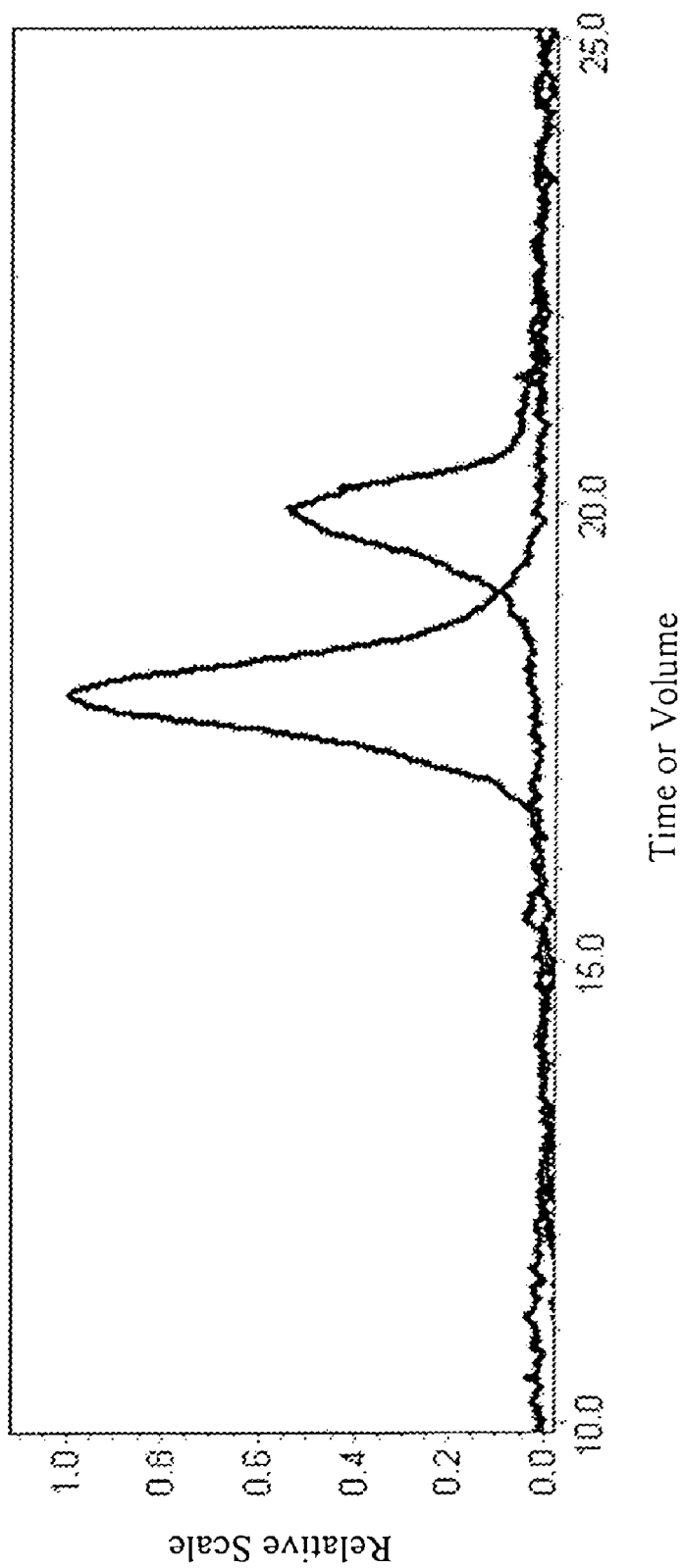
FIG. 2 depicts superimposed gel permeation chromatography curves of a homopolymer (right-hand peak) and a diblock co-polymer (left-hand peak) made according to the present invention.

The reactions shown in Reaction Scheme 2 and resulting GPC curves (see FIG. 2) demonstrate the ability of the present invention to fabricate co-polymers. Moving left-to-right across Reaction Scheme 2, in a first reaction, a β-polypeptide homopolymer was fabricated from compound 6 (see the Examples). The resulting homopolymer, shown in the middle of Reaction Scheme 2 had a molecular weight (Mn) of 2,500, and a PDI of 1.13). In FIG. 2, the resulting GPC curve for the homo-polymer is the right-hand peak.

Alternatively, a reactive terminal end-group can be used for terminal functionalization of the polymer or a different monomer can be introduced to yield a co-polymer. As shown in the right-hand portion of Reaction Scheme 2, additional monomer was added to the on-going polymerization to alter the ultimate molecular weight of the resulting polymer. The GPC curve of the resulting "m+n" co-polymer is the left-hand peak in FIG. 2. The "m+n" co-polymer shown in Reaction Scheme 2 had the following characteristics: Mn=17,300, PDI=1.23. The increased molecular weight of the "m+n" co-polymer of Reaction Scheme 2 as compared to the homopolymer of Reaction Scheme 2 is readily apparent by the leftward shift of the GPC peak of the co-polymer as compared to the GPC peak for the homopolymer. The comparability of the PDIs is also apparent as evidenced by the widths of the two peaks, which are quite similar (PDI=1.13 for the homopolymer, 1.23 for the co-polymer). These data are significant because they demonstrate that the present invention can be used to fabricate β-peptides of vastly different molecular weights (homopolymers, co-polymers, and terminally-functionalized polymers) in a controlled fashion (and without significantly increasing the polydispersity of the resulting polymers). In short, the exemplary reaction depicted in Reaction Scheme 2 yields a relatively small homopolymer and a comparatively far larger co-polymer, yet the PDI's for both products are very similar. See the Examples for a further discussion.

The present inventive reaction is both highly flexible and robust. Unlike past approaches, which are very sensitive to solvent effects and impurities, the present reaction will proceed using a host of low-cost initiators and solvents. The reaction is also robust and tolerant of impurities.

For example, polymerization of cyclooctyl-β-lactam was also tested in the presence of up to 20% mol of water or benzyl amine. The molecular weight and the PDI of the resulting polymers were unaffected relative to analogous reactions without the added water or benzyl amine. See Table 2. In the polymerization of compound 6, using the method of the present invention, product having a PDI less than 1.5 were obtained under a host of less-than-ideal conditions. The general reaction is shown in Reaction Scheme 3:

Reaction Scheme 3

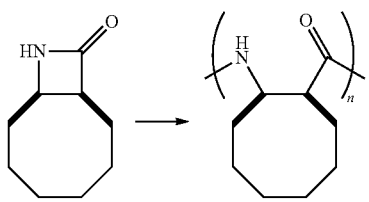

β-polypeptides were fabricated according to Reaction Scheme 3 using bicyclic β-lactam ring-opening anionic polymerization in common solvents including dichloromethane, tetrahydrofuran, and dimethylsulfoxide. The reaction can be initiated using common base initiators, including (without limitation) KOtBu, LiN(TMS)$_2$, and MeONa (in tetrahydrofuran).

Another distinct advantage of the present invention is that it allows a host of functional groups to be incorporated into the resulting polymer (either during the polymerization itself or via subsequent reactions involving reactive side groups post-polymerization.) For example, the β-lactam monomers can include functional groups on the side chains that are hydrophilic, hydrophobic, anionic, cationic, etc. The ratios of these various side chains within the final polymer can be controlled by controlling the relative amounts of each monomer in the co-polymerization reaction. The hydrophobic and cationic co-polymers, which are shown in the Examples, are particularly noteworthy because these side chains contribute to the antibacterial functionality of the polymers. Of course, the side chains can be manipulated to optimize any other desired property of the resulting polymer, be it solubility, biological activity, etc.

Additional monocyclic and bicyclic β-lactam monomers that have been fabricated and polymerized are shown in Reaction Scheme 4 (bicyclic monomers) and Reaction Scheme 5 (monocyclic monomers):

Reaction Scheme 4

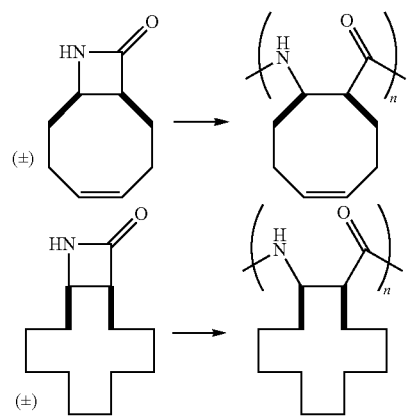

Reaction Scheme 5

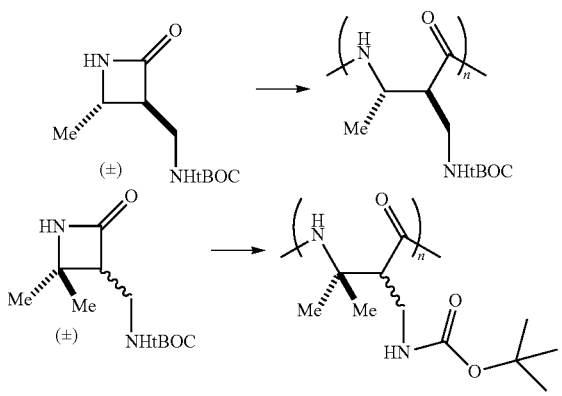

Reaction Scheme 4 illustrates the polymerization of bicyclic β-lactam monomers. Shown in the Reaction Scheme 4 are monomers that include a fused cyclooctene ring and a fused cyclododecane ring. Reaction Scheme 5 illustrates the polymerization of di- and tri-substituted monocyclic β-lactam monomers. The resulting polymers shown in Reaction Schemes 4 and 5 are obtained in high-yield (>90%), with very low molecular weight distributions (PDI's <1.5). See the Examples for further details.

Not all β-lactam-containing monomers will yield soluble products. Note, however, that the invention explicitly encompasses methods that yield soluble or insoluble polymeric products. For example, the following two β-lactam-containing monomers yield insoluble polymers when polymerized according to the present invention:

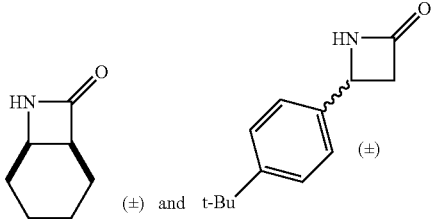

(See the Examples for a complete recitation of the reaction specifics.) Of particular note, however, is that all of these monomers can be readily polymerized in CH$_2$Cl$_2$ or THF, and the resulting polymers have very small PDIs, generally <1.5.

The synthetic route described herein is highly useful because a number of β-peptides and related compounds have been shown to be antimicrobial. See, for example, the Gellman et al. patents noted in the Background section. Thus, the present inventive method provides a new and robust route to making large quantities of β-peptides for medicinal use.

Additionally, the present invention is useful because it provides a versatile method to polymerize β-lactam-containing monomers under controlled conditions. The resulting polymers can then be used for systematic probing of a large array of polymer structures. For example, the present method allows systematic fabrication of homopolymers of known molecular weight and polydispersity. The method also allows for the systematic fabrication of random and block co-polymers using different combinations of co-monomers, monocyclic and bicyclic, including, without limitation, the following β-lactam-containing monomers:

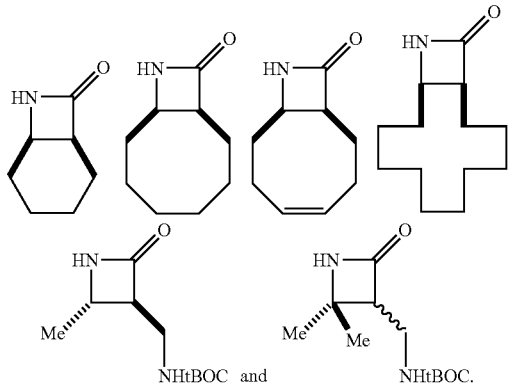

As a result, a whole host of β-peptides can be fabricated systematically, in molecular weights up to and greater than 20 kDa, including homopolymers, for example:

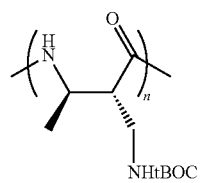

random co-polymers, for example:

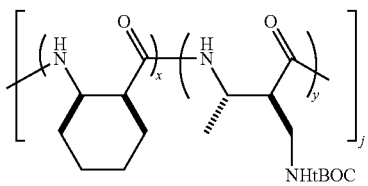

and block co-polymers, for example:

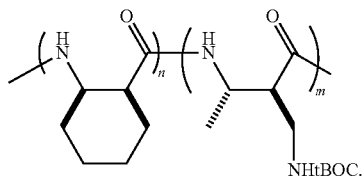

Further still, because the present method provides a systematic route to fabricating β-peptides, it also provides a robust means to optimize desired biological activities of β-peptides. In the past, this could only be done via step-wise, residue-by-residue synthesis—a extraordinarily laborious and time-consuming approach. In contrast, for example, the present method was used to synthesize a series of β-peptide homopolymers and co-polymers, which were then tested for antibacterial activity. Selected examples are shown in Table 1:

TABLE 1

Minimum Inhibitory Concentrations and Hemolytic Concentrations (HC$_{50}$)

| Min. Inhibitory Conc. (MIC) Against: | | | |
|---|---|---|---|
| E. coli | 200 µg/mL | 100 µg/mL | 25 µg/mL |
| B. subtilis | 12.5 µg/mL | 6.25 µg/mL | 6.25 µg/mL |
| S. aureus | 12.5 µg/mL | 25 µg/mL | 50 µg/mL |
| Conc for 50% lysis of human red blood cells | | | |
| (HC$_{50}$) | >1000 µg/mL | 100 µg/mL | n/a |

As can be seen from Table 1, the left-most polymer exhibited antimicrobial activity against *E. coli*, *B. subtilis*, and *S. aureus*, with MIC values of 200 µg/mL, 12.5 µg/mL, and 12.5 µg/mL, respectively, while at the same time exhibiting a vastly higher hemolytic concentration ($HC_{50}$), greater than 1,000 μg/mL. In other words, at concentrations where this compound is effective to inhibit the growth of *E. coli, B. subtilis*, and *S. aureus*, it exhibits very little hemolysis. (See the Examples for complete experimental details on how the values obtained in Table 1 were generated.) Thus, the present invention can be used to synthesize β-polypeptides that have desirable biological properties, such as antimicrobial activity. The invention is, in effect, an general purpose and robust method to synthesize large quantities of β-polypeptides under mild and controllable conditions.

If the ultimate product is to be incorporated into a pharmaceutical composition, the composition is preferably formulated by means generally known the industry. Thus, pharmaceutical compositions according to the present invention comprise an effective amount of a β-amino acid-containing polypeptide or a pharmaceutically acceptable salt thereof together with a pharmaceutically acceptable carrier. Optionally, other therapeutically active substances or accessory agents may be included in addition to the β-polypeptide or the salt thereof. The pharmaceutical compositions of the invention comprise an amount of β-polypeptide or a pharmaceutically acceptable salt thereof that is effective to treat a bacterial, viral, or fungal infection in a mammal suffering therefrom (including humans). The carrier must be pharmaceutically acceptable in the sense of being compatible with the other ingredients in the particular composition and not deleterious to the recipient of the composition. The compositions include those suitable for oral, topical, rectal or parenteral (including subcutaneous, intramuscular, intradermal and intravenous) administration.

In a particular aspect, the pharmaceutical compositions comprise the active ingredient (a β-polypeptide or a pharmaceutically acceptable salt thereof) presented in unit dosage form. The term "unit dosage" or "unit dose" designates a predetermined amount of the active ingredient sufficient to be effective to treat each of the indicated activities. Preferred unit dosage formulations are those containing a daily dose, daily sub-dose, or an appropriate fraction thereof, of the administered active ingredient.

The pharmaceutical compositions may be prepared by any of the methods well known in the art of pharmacy. All methods include the step of bringing the active ingredient into association with a carrier which constitutes one or more accessory ingredients. In general, the compositions are prepared by uniformly and intimately bringing the active ingredient into association with a liquid or solid carrier and then, if necessary, shaping the product into the desired unit dosage form.

Compositions of the present invention suitable for oral administration may be presented as discrete unit dosages, e.g., as capsules, cachets, tablets, boluses, lozenges and the like, each containing a predetermined amount of the active ingredient; as a powder or granules; or in liquid form, e.g., as a collyrium, suspension, solution, syrup, elixir, emulsion, dispersion and the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients or excipients, e.g., binders, lubricants, inert diluents, surface-active or dispersing agents. Molded tablets may be made by molding in a suitable machine a mixture of the powdered active compound with any suitable carrier.

Compositions suitable for parenteral administration conveniently comprise a sterile injectable preparation of the active ingredient in, for example, a solution which is preferably isotonic with the blood of the recipient. Useful formulations also comprise concentrated solutions or solids containing the active ingredient which upon dilution with an appropriate solvent give a solution suitable for parenteral administration. The parenteral compositions include aqueous and non-aqueous formulations which may contain conventional adjuvants such as buffers, bacteriostats, sugars, thickening agents and the like. The compositions may be presented in unit dose or multi-dose containers, for example, sealed ampules and vials.

Compositions suitable for topical or local application (including ophthamological administration) comprise the active ingredient formulated into pharmaceutically-acceptable topical vehicles by conventional methodologies. Common formulations include drops, collyriums, aerosol sprays, lotions, gels, ointments, plasters, shampoos, transferosomes, liposomes and the like.

Compositions suitable for inhalation administration, for example, for treating bronchial infections, wherein the carrier is a solid, include a micronized powder or liquid formulation having a particle size in the range of from about 5 microns or less to about 500 microns, for rapid inhalation through the nasal or oral passage from a conventional inhalation squeeze or spray container. Suitable liquid nasal compositions include conventional nasal sprays, nasal drops and the like, of aqueous solutions of the active ingredient and optional adjuvants.

In addition to the aforementioned ingredients, the compositions of this invention may further include one or more optional accessory ingredients(s) utilized in the art of pharmaceutical formulations, e.g., diluents, buffers, flavoring agents, colorants, binders, surfactants, thickeners, lubricants, suspending agents, preservatives (including antioxidants) and the like.

The amount of active ingredient required to be effective for each of the indicated activities will, of course, vary with the individual mammal being treated and is ultimately at the discretion of the medical or veterinary practitioner. The factors to be considered include the species and sex of the mammal, the ailment being treated, the route of administration, the nature of the formulation, the mammal's body weight, surface area, age and general condition, and the particular compound to be administered.

In general, the pharmaceutical compositions of this invention contain from about 0.5 to about 500 mg and, preferably, from about 5 to about 350 mg of the active ingredient, preferably in a unit dosage form, for each of the indicated activities. However, a suitable effective dose is in the range of about 0.1 to about 200 mg/kg body weight per day, preferably in the range of about 1 to about 100 mg/kg per day, calculated as the non-salt form of the β-polypeptide. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal, a dose range would be about 7.5 to about 1500 mg per day, and a typical dose would be about 800 mg per day. If discrete multiple doses are indicated, treatment might typically be 200 mg of the active agent, twice per day.

In topical formulations, the subject compounds are preferably utilized at concentrations of from about 0.1% to about 5.0% by weight.

EXAMPLES

The following Examples are included to provide a more complete understanding of the invention disclosed and claimed herein. The Examples do not limit the scope of the invention in any fashion.

Example 1

Monomer and Co-Initiator Synthesis:

Synthesis of Coinitiator (2):

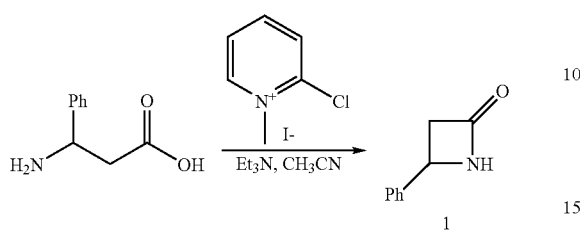

Compound 1 was prepared using the method of Huang and coworkers (Huang, H.; Iwasawa, N.; Mukaiyama, T. (1984) "A Convenient Method for the Construction of β-Lactam Compounds from β-Amino Acids Using 2-Chloro-1-Methyl Pyridinium Iodide as Condensing Reagent," *Chem. Lett.* 1465-1466). In a 1 L round-bottomed flask was combined DL-3-amino-3-phenyl propionic acid (0.007 mol, 1.156 g), 2-chloro-1-methyl pyridinium iodide (1.1 eq., 0.0077 mol, 1.74 g), acetonitrile (700 mL) and triethylamine (2.2 eq., 0.0154 mol, 2.15 mL). The reaction was stirred under nitrogen and heated to reflux overnight. The solvent was removed by rotary evaporation and the crude product was purified by column chromatography in 1:1 hexanes:ethyl acetate. Yield: 0.808 g, 40%. $^1$H NMR (CDCl$_3$) δ 2.84-2.9, m, 1 H; 3.40-3.48, m, 1 H; 4.71-4.74, m, 1 H; 6.38, br s, 1 H; 7.2-7.4, m, 5 H.

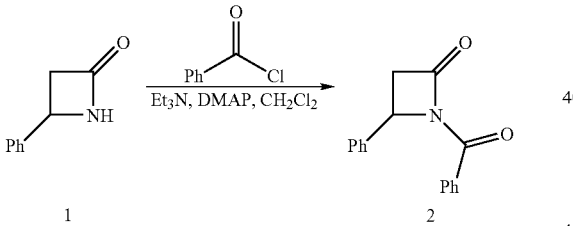

Compound 2 was prepared using the method of Park and coworkers (Park, H.; Hepperle, M.; Boge, T. C.; Himes, R. H.; Georg, G. I. (1996) "Preparation of Phenolic Paclitaxel Metabolites," *J. Med. Chem.* 39:2705-2709). In a 25 mL round-bottomed flask was combined (1) (0.0017 mol, 0.250 g), triethylamine (4.63 eq., 0.0073 mol, 1.02 mL), dry methylene chloride (6.3 mL), and dimethylamino pyridine (10 mol %, 1.7 E-4 mol, 0.021 g). The reaction was cooled to 0° C. and benzoyl chloride (3.33 eq., 0.0057 mol, 0.66 mL) was added. The reaction was warmed to room temperature and stirred for 1 h. The reaction was quenched with saturated ammonium chloride (30 mL) and diluted with methylene chloride (150 mL). The reaction mixture was then washed with NaHCO$_3$ and then with brine. The organic portion was dried over MgSO$_4$ and the solvent removed by rotary evaporation. The crude product was purified by column chromatography in 1:1 hexanes:ethyl acetate. Yield: 0.320 g, 75%. $^1$H NMR (CDCl$_3$) δ 3.094, dd J=16.5, 3.9 Hz, 1 H; 3.528, dd J=16.5, 6.9 Hz, 1 H; 5.29, m, 1 H; 7.26-7.60, m, 8 H; 8.01-8.04, m, 2 H. $^{13}$C {$^1$H} NMR (CDCl$_3$) δ 44.23, 51.56, 125.77, 127.99, 128.26, 128.73, 129.75, 131.68, 133.22, 137.99, 163.91, 165.65.

FTIR (ATR): 1675 cm$^{-1}$, 1735 cm$^{-1}$, 1778 cm$^{-1}$, 1795 cm$^{-1}$. MS-ESI: m/z=525.2 [2 M+Na]$^+$.

β-Lactam 3 was synthesized according to the literature precedent. See Parsons, P. J.; Camp, N. P.; Underwood, J. M.; Harvey, D. M. (1996) "Tandem Reactions of Anions: A Short and Efficient Route to±Anatoxin-a," *Tetrahedron*, 52:11637-11642.

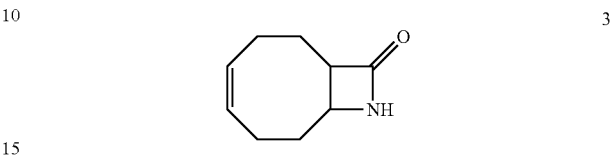

β-Lactams 4 and 5 were synthesized according to the literature precedent. See Dener, J. M.; Fantauzzi, P. P.; Kshirsagar, T. A.; Kelly, D. E.; Wolfe, A. B. (2001) "Large-Scale Synthesis of FMOC-Protected Non-Proteogenic Amino Acids: Useful Building Blocks for Combinatorial Libraries," *Organic Process Research and Development*, 5:445-449.

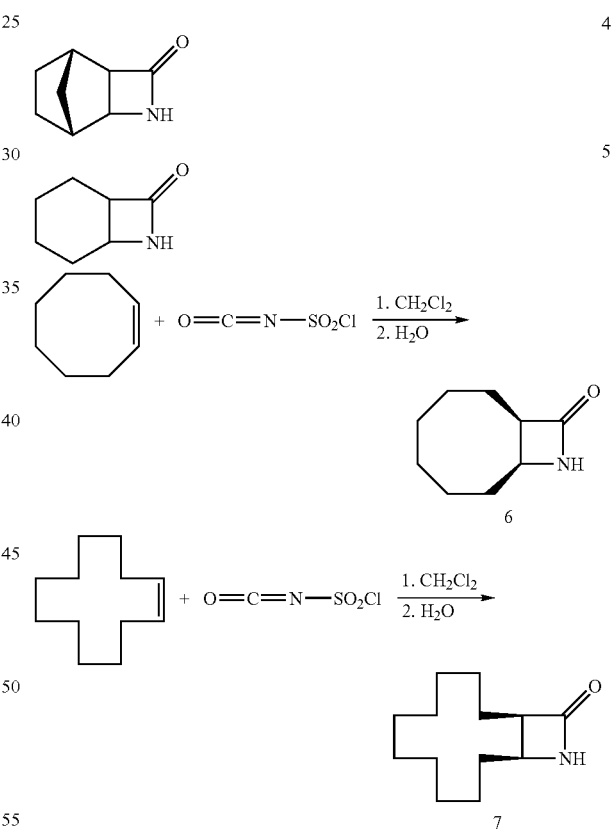

Compounds 6 and 7 were prepared using the same general method used for compounds 4 and 5.$^4$ For compound 6: In an oven-dried 25 mL round-bottomed flask was combined cis-cyclooctene (0.023 mol, 3 mL) and dry CH$_2$Cl$_2$ (3.3 mL). The reaction was cooled to 0° C. and stirred under N$_2$. A solution of chlorosulfonyl isocyanate (CSI) (1 eq., 0.023 mol, 2 mL) in dry CH$_2$Cl$_2$ (1.1 mL) was made and added dropwise to the cooled reaction mixture. The reaction was allowed to stir at 0° C. for 1 h and then warmed to room temperature overnight. The reaction was then re-cooled to 0° C. and quenched by adding water. The quenched reaction mixture was added to a suspension of Na$_2$SO$_3$ (1.45 g) in water (4.3 mL), keeping the temperature below 25° C. and the pH between 5 and 7 using 2 M NaOH. The reaction was allowed to warm to room temperature overnight. The layers were separated and the aqueous portion was extracted with EtOAc. The combined organic portions were dried over MgSO$_4$ and the solvent removed by rotary evaporation. The crude product can be purified by column chromatography (EtOAc as eluent) or recrystallization from CH$_2$Cl$_2$ and hexanes. Yield=3.6 g, 51%. $^1$H NMR (CDCl$_3$) δ 1.30-1.99, m, 12 H; 3.01-3.10, m, 1 H; 3.62-3.69, m, 1 H; 5.86, br s, 1 H. $^{13}$C {$^1$H} NMR (CDCl$_3$) δ 21.34, 25.25, 25.69, 27.24, 28.59, 27.72, 53.58, 171.0. FTIR (ATR): 1725 cm$^{-1}$, 3205 cm$^{-1}$. MS-EI: m/z=154.1 [M+H]$^+$.

For Compound 7: In an oven-dried round-bottomed flask was combined cyclododecene (0.023 mol, 3.97 mL) and CSI (1 eq., 0.023 mol, 2 mL). The reaction was put under nitrogen and heated to 50° C. overnight. The reaction was allowed to cool, diluted with CH$_2$Cl$_2$, and quenched by adding water. The quenched reaction was added to a suspension of Na$_2$SO$_3$ (1.6 g) in water (5 mL), keeping the temperature below 25° C. and the pH between 5 and 7 using 2 M NaOH. The reaction was allowed to warm to room temperature overnight and then the layers were separated. The aqueous layer was extracted twice with EtOAc and the combined organic layers were dried over MgSO$_4$ and the solvent was removed by rotary evaporation. The crude product was purified by recrystallization from CH$_2$Cl$_2$ and hexanes. Yield=0.47 g, 10%. $^1$H NMR (CDCl$_3$) δ 1.30-1.80, m, 20 H; 3.10-3.16, m, 1 H; 3.64-3.70, m, 1 H; 6.11, br s, 1 H. $^{13}$C {$^1$H} NMR (CDCl$_3$) δ 2.24, 22.84, 23.22, 24.90, 27.62, 27.83, 28.12, 28.21, 29.20, 53.20, 54.20, 171.78. FTIR (ATR): 1740 cm$^{-1}$, 3204 cm$^{-1}$. MS-ESI: m/z=232.3 [M+Na]$^+$.

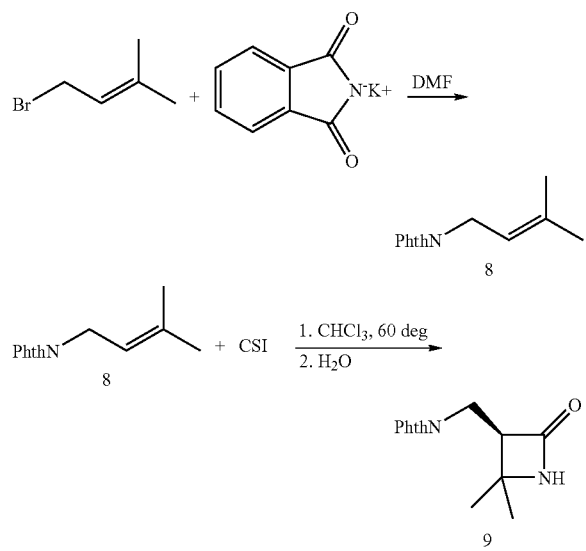

For Compound 8: In a 500 mL round-bottomed flask was combined potassium phthalimide (1.5 eq., 0.067 mol, 12.33 g) and DMF (140 mL). The reaction was stirred and a solution of 1-chloro-3-methyl-2-butene (1 eq., 0.044 mol, 5 mL) in DMF (95 mL) was added to the reaction. The flask was put under N$_2$ and heated to 60° C. overnight. The reaction was allowed to cool and then poured into 1400 mL ice and water with vigorous stirring. The stirring was continued until the ice melted. The resulting white precipitate was isolated by filtration. The wet solid was dissolved in CH$_2$Cl$_2$ and the layers were separated. The organic portion was dried over MgSO$_4$ and the solvent removed by rotary evaporation to give crude product. The product was purified by recrystallization from CH$_2$Cl$_2$ and hexanes. Yield=7.2 g, 76%.

Compound 9 was prepared from Compound 8 in the following manner: In a 100 mL round-bottomed flask was placed Compound 8 (1 eq., 0.033 mol, 7 g). It was dissolved in as little dry CH$_2$Cl$_2$ as possible and the flask put under N$_2$ and cooled to 0° C. CSI (1 eq., 0.033 mol, 2.9 mL) was added to the flask and the reaction allowed to stir and warm to room temperature for 1-2 days. The reaction was quenched by adding water and the quenched reaction mixture was added to a suspension of Na$_2$SO$_3$ and Na$_2$HPO$_4$ (5 g each) in water (140 mL). The pH was maintained between 5 and 7 using 2 M NaOH and the reaction was allowed to stir at room temperature for 2 days. The layers were then separated and the aqueous portion was extracted twice with CH$_2$Cl$_2$. The combined organic portions were dried over MgSO$_4$ and the solvent removed by rotary evaporation. The crude product was recrystallized from CH$_2$Cl$_2$ and hexanes. Yield=6.2 g, 73%. $^1$H NMR (CDCl$_3$) δ 1.45, s 3 H; 1.47, s, 3 H; 3.41, td J=8.1, 0.9 Hz, 1 H; 3.91, dd J=14.1, 8.1 Hz, 1 H; 4.05-4.13, m, 1 H; 6.44 br s, 1 H; 7.71-7.74, m, 2 H; 7.84-7.87, m, 2 H. $^{13}$C {$^1$H} NMR (CDCl$_3$) δ 14.31, 21.15, 23.38, 25.58, 34.31, 55.18, 56.66, 60.48, 123.52, 132.11, 134.17, 167.47, 168.06. FTIR (ATR): 1715 cm$^{-1}$, 1741 cm$^{-1}$, 3200 cm$^{-1}$. MS-ESI: m/z=259.3 [M+H]$^+$.

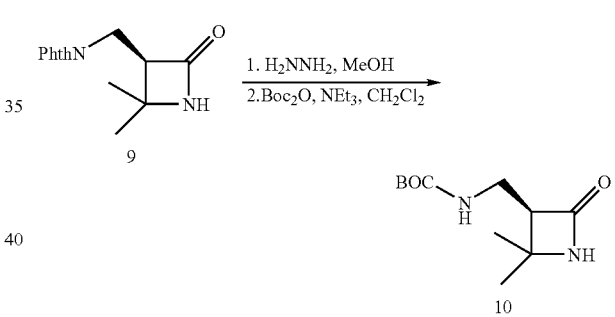

Compound 10 was prepared from Compound 9 in the following manner: In a 250 mL round-bottomed flask was suspended Compound 9 (1 eq., 0.024 mol, 6.2 g) in methanol (36 mL). Hydrazine (3 eq., 0.072 mol, 2.26 mL) was added and the reaction was allowed to stir at room temperature under N$_2$ overnight. The methanol was removed by rotary evaporation and the resulting solid was triturated with chloroform. The solvent was removed from the chloroform washings by rotary evaporation. The residue was placed in a 500 mL round-bottomed flask with CH$_2$Cl$_2$ (200 mL). Triethylamine (1.1 eq., 0.053 mol, 7.39 mL) was then added followed by a solution of di-tert-butyl-dicarbonate (BOC$_2$O) (1.1 eq., 0.053 mol, 11.6 g) in CH$_2$Cl$_2$ (100 mL). The reaction was allowed to stir at room temperature overnight and then washed twice with 2 M HCl, twice with 2 M NaOH, and once with brine before being dried over MgSO$_4$ and stripped by rotary evaporation to yield crude product. The product was purified by column chromatography using EtOAc as eluent. Yield=2.9 g, 53%. $^1$H NMR (CDCl$_3$) δ 1.40, s, 3 H; 1.44, s, 3 H; 1.45, s, 9 H; 2.97 app t J=7.8 Hz, 1 H; 3.29, m, 1 H; 3.58, m, 1 H; 5.10, br s, 1 H. $^{13}$C {$^1$H} NMR (CDCl$_3$) δ 22.92, 28.49, 28.68, 37.20, 54.83, 58.34, 79.61, 155.89, 169.32. FTIR (ATR):

1688 cm$^{-1}$, 1716 cm$^{-1}$, 1744 cm$^{-1}$, 3194 cm$^{-1}$, 3280 cm$^{-1}$. MS-ESI/EMM: m/z=Calc. 251.1372 [M+Na]$^+$. Meas. 251.1372 [M+Na]$^+$.

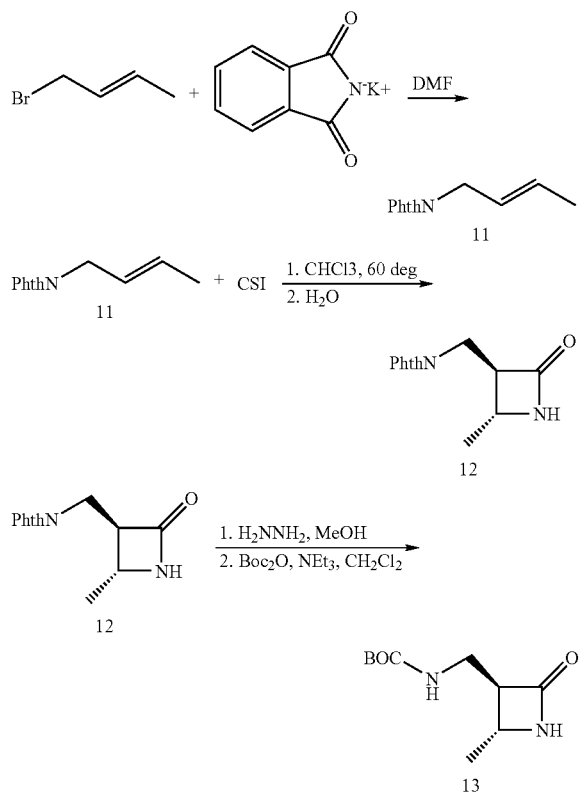

Compound 11: In a 2 L round-bottomed flask was combined potassium phthalimide (1.5 eq., 0.28 mol, 52 g) and DMF (400 mL). A solution of crotyl bromide (1 eq., 0.185 mol, 25 g) in DMF (300 mL) was then added and the reaction stirred at 60° C. overnight. The reaction was allowed to cool and then poured into 4000 mL ice and water with vigorous stirring. The stirring was continued until the ice melted. The resulting white precipitate was isolated by filtration. The wet solid was dissolved in CH$_2$Cl$_2$ and the layers were separated. The organic portion was dried over MgSO$_4$ and the solvent removed by rotary evaporation to give crude product. The product was purified by recrystallization from CH$_2$Cl$_2$ and hexanes. Yield=17.8 g, 56%.

Compound 12: In a 100 mL round-bottomed flask was placed Compound 11 (1 eq., 0.085 mol, 17 g). It was dissolved in as little dry CHCl$_3$ as possible and the flask put under N$_2$ and cooled to 0° C. CSI (1 eq., 0.033 mol, 2.9 mL) was added to the flask and the reaction allowed to stir and warm to room temperature, then heated to 60° C. for 4-5 days. The reaction was quenched by adding water and the quenched reaction mixture was added to a suspension of Na$_2$SO$_3$ and Na$_2$HPO$_4$ (40 g each) in water (700 mL). The pH was maintained between 5 and 7 using 2 M NaOH and the reaction was allowed to stir at room temperature for 2 days. The layers were then separated and the aqueous portion was extracted twice with CH$_2$Cl$_2$. The combined organic portions were dried over MgSO$_4$ and the solvent removed by rotary evaporation. The crude product was recrystallized from CH$_2$Cl$_2$ and hexanes. Yield=7.6 g, 38%. $^1$H NMR (CDCl$_3$) δ 1.32, d J=6 Hz, 3 H; 3.15 app t J=6.9 Hz, 1 H; 3.79-3.83, m, 1 H; 3.97, dd J=14, 9.6 Hz, 1 H; 4.14, dd J=14, 5.7 Hz, 1 H; 6.01, br s, 1 H; 7.72-7.77, m, 2 H; 7.84-7.88, m, 2 H. $^{13}$C {$^1$H} NMR (CDCl$_3$) δ 20.75, 36.62, 50.46, 57.12, 123.69, 132.11, 134.37, 167.07, 168.23. MS-ESI: m/z=267.2 [M+Na]$^+$.

Compound 13: In a 25 mL round-bottomed flask was suspended Compound 12 (1 eq., 0.0021 mol, 0.5 g) in methanol (10 mL). Hydrazine (5 eq., 0.0105 mol, 0.33 mL) was added and the reaction was allowed to stir at room temperature under N$_2$ overnight. The reaction was filtered on a frit and washed with copious amounts of methanol. The solvent was removed from the filtrate by rotary evaporation. The residue was placed in a 100 mL round-bottomed flask with CH$_2$Cl$_2$ (20 mL). Triethylamine (1.1 eq., 0.0057 mol, 0.8 mL) was then added followed by a solution of di-tert-butyl-dicarbonate (BOC$_2$O) (1.1 eq., 0.0057 mol, 1.25 g) in CH$_2$Cl$_2$ (10 mL). The reaction was allowed to stir at room temperature overnight and then washed twice with 2 M HCl, twice with 2 M NaOH, and once by brine before being dried over MgSO$_4$ and stripped by rotary evaporation to yield crude product. The product was purified by column chromatography using EtOAc as eluent. Yield=0.071 g, 16%. $^1$H NMR (CDCl$_3$) δ 1.37, d J=6 Hz, 3 H; 1.44, s, 9 H; 2.89, tdd J=6, 2.1, 0.9 Hz, 1 H; 3.48, m, 2 H; 3.64, qd J=6, 2.1 Hz, 1 H; 4.95, br s, 1 H; 6.06, br s, 1 H. $^{13}$C NMR (CDCl$_3$) δ 20.54, 28.55, 38.46, 48.84, 58.57, 79.89, 164.71, 168.99. MS-ESI/EMM: m/z=Calc. 237.1215 [M+Na]$^+$. Meas. 237.1208 [M+Na]$^+$.

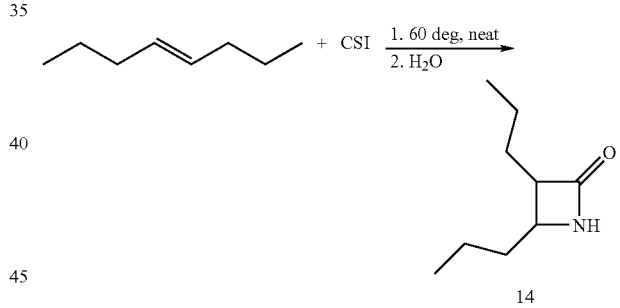

Compound 14: In a dry 25 mL round-bottomed flask was placed trans-4-octene (1 eq., 0.009 mol, 1.4 mL). CSI (1 eq., 0.009 mol, 0.78 mL) was added to the flask and the reaction allowed to stir at 60° C. overnight. The reaction was diluted with CH$_2$Cl$_2$ and then quenched by adding water. The quenched reaction mixture was added to a suspension of Na$_2$SO$_3$ and Na$_2$HPO$_4$ (1 g each) in water (20 mL). The pH was maintained between 5 and 7 using 2 M NaOH and the reaction was allowed to stir at room temperature overnight. The layers were then separated and the aqueous portion was extracted twice with CH$_2$Cl$_2$. The combined organic portions were dried over MgSO$_4$ and the solvent removed by rotary evaporation. The crude product was purified by column chromatography using 1:1 hexanes:EtOAc as eluent. Yield=0.38 g, 27%. $^1$H NMR (CDCl$_3$) δ 0.98, m, 6 H; 1.31-1.77, m, 8 H; 2.73, br t J=7.5 Hz, 1 H; 3.29, td J=6.9, 2.1 Hz, 1 H; 6.48, br s, 1 H. $^{13}$C NMR (CDCl$_3$) δ 14.11, 14.16, 19.90, 20.78, 30.89, 37.47, 55.38, 56.91, 171.83. MS-EI: m/z=156.2 [M +H]$^+$.

Synthesis of compound (15):

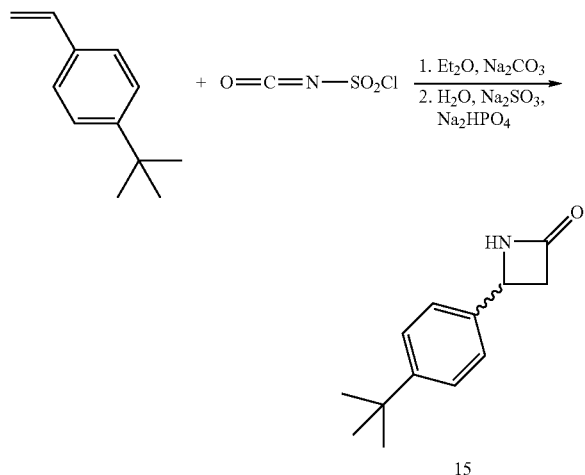

15

Compound 15 was prepared using a modified literature procedure. See Parsons, P. J.; Camp, N. P.; Underwood, J. M.; Harvey, D. M. (1996) "Tandem Reactions of Anions: A Short and Efficient Route to± Anatoxin-a." *Tetrahedron* 52: 11637-11642. In a 50 mL round-bottomed flask was combined 4-tert-butylstyrene (0.016 mol, 2.62 g) and dry diethyl ether (5 mL). The mixture was cooled to 0° C. and stirred under $N_2$. Chlorosulfonyl isocyanate (CSI) (1 eq., 0.016 mol, 2.32 g) was added dropwise to the cooled reaction mixture. The reaction was allowed to stir at 0° C. for 1 h and then warned to room temperature overnight. The reaction was then diluted with chloroform (20 mL), cooled to 0° C. and quenched by addition into a stirring aqueous solution (100 mL) of $Na_2SO_3$ (12 g) and $Na_2PO_4$ (14 g), keeping the temperature below 25° C. and the pH between 6 and 8 by additions of 2 M NaOH. The reaction was allowed to warm to room temperature overnight. The layers were separated and the aqueous portion was extracted with chloroform. The combined organic portions were dried over $MgSO_4$ and the solvent removed by rotary evaporation. The crude product was recrystallized from diethyl ether. Yield: 1.8 g, 54%. $^1$H NMR (300 MHz, $CDCl_3$, ppm) δ 1.32, s, 9 H; 2.90, ddd J=15, 2.5, 1.1 Hz, 1 H; 3.43, ddd J=15, 5.1, 2.4 Hz, 1H; 4.70, dd J=5.4, 2.7 Hz, 1 H; 6.1, s, 1H; 7.37, app. dd J=33, 10.8 Hz, 4 H. MS (ESI)=429.5 [2M+Na]$^{+}$ Example 2

Polymer Synthesis

Materials:

All reagents were obtained from Aldrich (Milwaukee, Wis.) and used as received. $CH_2Cl_2$ and THF were distilled under reduced pressure over $CaH_2$.

Instrumentation:

$^1$H (300 MHz) and $^{13}$C (75 MHz) NMR spectra were obtained on a Bruker AC+ 300 NMR spectrometer. Gel Permeation Chromatography (GPC) was performed using a Shimadzu LC-10AD liquid chromatography (HPLC) pump equipped with Wyatt miniDawn and Optilab rex detectors. The mobile phase was THF with a flow rate of 1 mL/min. Separations were performed using TSK-GEL column set (2×GMH$_{HR}$-H).

Homopolymerization of 6:

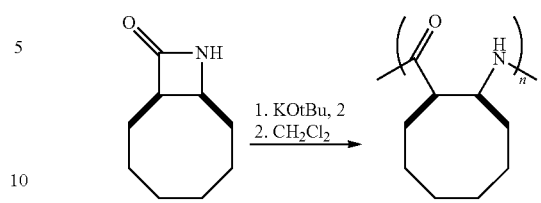

Polymerization of 6 is a representative procedure for the polymerizations of β-lactam monomers 3-7, 10, and 13-15. Any experimental and observational exceptions will be noted. In a 7 mL glass vial, under inert atmosphere, was combined 6 (1 mmol, 153 mg), potassium tert-butoxide (KOtBu, 0.045 mmol, 5 mg) as base to deprotonate a certain fraction of the monomer, and 2 (0.02 mmol, 5 mg) as coinitiator and as the means to control the molecular weight. Monomer to coinitiator ratios ranging from 1/10 to 1/250 were successfully employed depending on the targeted molecular weight. The mixture was dissolved by addition of dichloromethane ($CH_2Cl_2$, 1 mL), or THF (1 mL) and kept under room temperature for 0.5 to 4 hours depending on the monomer to coinitiator ratio where higher ratios require longer polymerization times. Then the mixture was opened to air, the polymer was precipitated into pentane (10 mL), and isolated by centrifuging and removing the supernatant. Polymer was dried overnight under reduced pressure at room temperature. The isolated yield was 95% (146 mg). $^1$H NMR (300 MHz, $CDCl_3$, ppm) δ 1.10-2.10, broad s, 12 H; 2.15-3.10, broad m, 1 H; 4.2-5.0, broad m, 1 H; 7.43, m, end-group low-resolution peak; 7.89, m, end-group low-resolution peak. $M_n$=5840 g/mol, polydispersity index (PDI) =1.02 (dn/dc=1.37).

Alternative Compounds as Base Initiator:

The general procedure described in the above paragraph was employed by replacing KOtBu with an alternative base including lithium bis(trimethylsilyl)amide (LiN(TMS)$_2$), potassium bis(trimethylsilyl)amide (KN(TMS)$_2$, sodium methoxide (NaOEt, in tetrahydrofuran). All of the above mentioned bases resulted in low PDI polymers with molecular weights in close approximation to targeted molecular weights.

Less Preferred Initiators:

The following metal complexes Sc(N(TMS)$_2$)$_3$, Al$_2$(N (Me)$_2$)$_6$, Al(N(TMS)$_2$)$_3$, Zn(N(TMS)$_2$)$_2$, Sn(N(TMS)$_2$)$_2$, and CpTi(N(Me)$_2$)$_2$Cl were employed in the above described general polymerization procedure and initial results showed the reactions resulted in the recovery of more than 90 mol% of the monomers. Little polymeric product was obtained. Thus, these metal complexes are not preferred for use in the present invention.

Alternative Homopolymerization of 6:

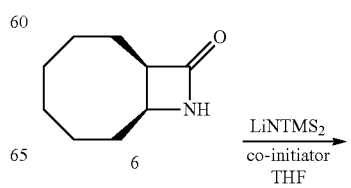

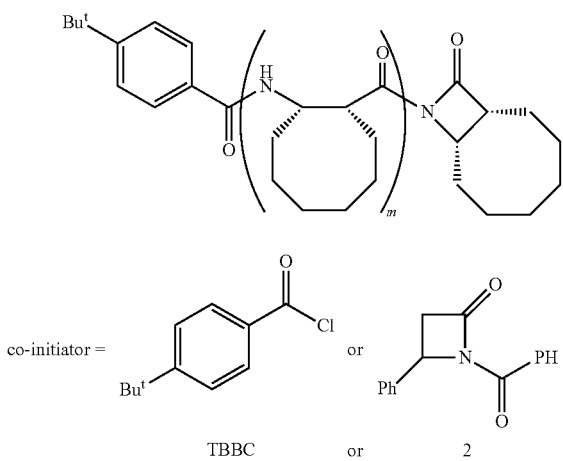

had slightly broader polydispersity. Similar increased broadening of the polydispersity was observed when KOtBu and NaOMe(THF) were used as the base. The use of heterogeneous KH as a base yielded a polymer with PDI>2. Adding water or amine (20 mol %) to the reaction yields a polymer product with a relatively small molecular weight, but without any broadening of the PDI of the product (<2).

Both water and amine are known to poison other anionic polymerization reactions. Polydispersity broadened (from about 1.06 to 1.27) when the polymerization reaction is allowed to proceed for several hours.

A host of monomer, co-initiator, solvent, and base combinations were fabricated in the same fashion as reported here. The results are summarized in Table 2.

TABLE 2

Polymerization results for monomers 1-5 ([monomer]/[co-initiator] = 30):

| Monomer | Co-initiator | Base | Solvent | Yield, % | $M_n$ | PDI |
|---|---|---|---|---|---|---|
| 6 | TBBC | LiN(SiMe$_3$)$_2$ | THF | 96 | 4,900 | 1.05 |
| 6 | Cmpd 2 | LiN(SiMe$_3$)$_2$ | THF | 95 | 4,700 | 1.12 |
| 6 | TBBC | LiN(SiMe$_3$)$_2$ | CH$_2$Cl$_2$ | 93 | 5,100 | 1.14 |
| 6 | TBBC | KOtBu | THF | 96 | 5,400 | 1.11 |
| 6 | Cmpd 2 | KOtBu | CH$_2$Cl$_2$ | 95 | 4,900 | 1.15 |
| 6 | TBBC | KH | THF | 94 | 6,800 | 2.40 |
| 6 | TBBC | MeONa | THF | 97 | 5,100 | 1.14 |
| 6 | TBBC | MeONa | MeOH | No reaction | | |
| 6 | Cmpd 2 | NaOH | THF/H$_2$O (1:1) | No reaction | | |
| 6 | Cmpd 2 | LiN(SiMe$_3$)$_2$ | THF/BnNH$_2$ (20% mol to monomer) | 92 | 5,200 | 1.12 |
| 6 | Cmpd 2 | LiN(SiMe$_3$)$_2$ | THF/H$_2$O (20% mol to monomer) | 90 | 4,950 | 1.14 |
| 6 | Cmpd 2 | LiN(SiMe$_3$)$_2$ | THF/H$_2$O (1:20) | 93 | 4,500 | 1.16 |
| 5 | TBBC | LiN(SiMe$_3$)$_2$ | THF | 97 | Insoluble in THF | |
| 7 | TBBC | LiN(SiMe$_3$)$_2$ | THF | 95 | 7,300 | 1.10 |
| 10 | TBBC | LiN(SiMe$_3$)$_2$ | THF | 98 | 5,200 | 1.06 |
| 13 | TBBC | LiN(SiMe$_3$)$_2$ | THF | 98 | 5,900 | 1.10 |

Here, the reaction takes place in THF at ambient temperature in the presence of a base [LiN(SiMe$_3$)$_2$] and a co-initiator (as shown either 4-tert-butyl benzoyl chloride (TBBC) or compound 2). The appropriate amounts of the monomer and co-initiator were mixed together in THF, whereupon a solution of base was added to the mixture in one portion. After 1 hour, the polymer product was precipitated by adding pentane to the reaction solution. The product was isolated by centrifugation and dried under high vacuum. 4-Tert-butyl benzoyl chloride or the N-benzoyl-β-lactam (compound 2) were used as co-initiators.

Reactions using 4-tert-butyl benzoyl chloride as the co-initiator showed narrower polydispersity of the polymer product obtained as compared to reactions using compound 2 as the co-initiator. Other bases (KOtBu, KH, NaOMe, NaOH) and alternative solvents and solvent mixtures (CH$_2$Cl$_2$, MeOH, THF/H$_2$O) were also tried for this reaction. Polymerization readily occurred in CH$_2$Cl$_2$, but the resulting polymer This Example demonstrates a general approach for preparing β-polypeptides bearing side chains having polar functional groups.

Homopolymerization of Other β-Lactam-Containing Monomers:

Using the approach recited in the immediately prior Example, the following bicyclic and monocyclic monomers were also successfully polymerized:

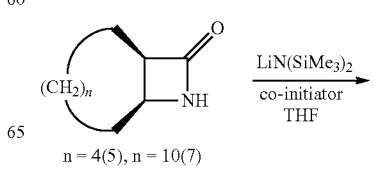

n = 4(5), n = 10(7)

-continued

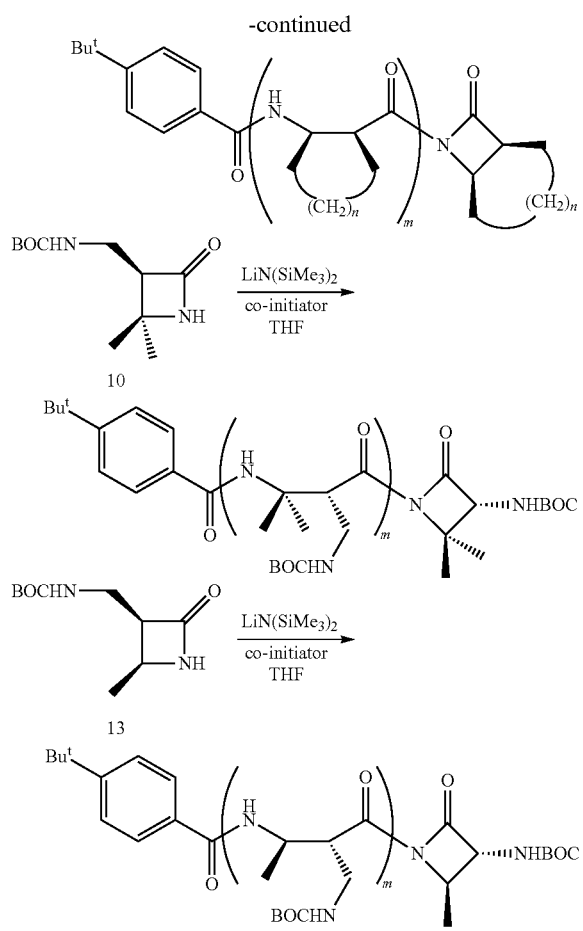

Homopolymerization of 3:

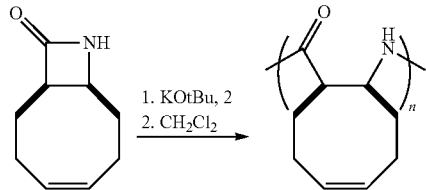

In a 7 mL glass vial, under inert atmosphere, was combined 3 (0.2 mmol, 30 mg), potassium tert-butoxide (KOtBu, 0.0045 mmol, 0.5 mg), and 2 (0.002 mmol, 0.5 mg). The polymer was isolated as described above for poly(6). The isolated yield was 92% (142 mg). $^1$H NMR (300 MHz, CDCl$_3$, ppm) δ 1.30-3.20, broad m, 9 H; 4.20-4.80, broad s, 1 H; 5.40-5.80, broad s, 2 H; 7.43, m, end-group low-resolution peak; 7.89, m, end-group low-resolution peak. $M_n$=16,000 g/mol, PDI=1.2 (for dn/dc=1.37). The GPC curve for this polymer is shown in FIG. 1.

Homopolymerization of 5:

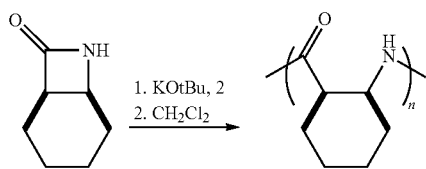

The isolated yield was 90% (139 mg). $^1$H NMR (300 MHz, CDCl$_3$, ppm) δ 1.10-2.05, broad m, 8 H; 2.53, s, 1 H; 3.98, s, 1 H; 7.43, m, end-group low-resolution peak; 7.89, m, end-group low-resolution peak. The resulting polymer was mostly insoluble in THF.

Homopolymerization of 10:

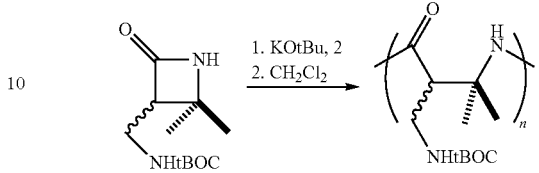

In a 7 mL glass vial, under inert atmosphere, was combined 10 (0.2 mmol, 45 mg), potassium tert-butoxide (KOtBu, 0.02 mmol, 2 mg), and 2 (0.014 mmol, 3.5 mg). The polymer was isolated as described above for poly(6). The isolated yield was 95% (44 mg). $^1$H NMR (300 MHz, CDCl$_3$, ppm) δ 1.00-1.80, broad s, 9 H; 2.05-3.70, overlapping resonances, broad m, 9 H; 7.50, m, end-group low-resolution peak; 7.94, m, end-group low-resolution peak. $M_n$=10,400 g/mol, PDI=1.16 (for dn/dc=1.37). The t-BOC protected primary amine groups on this polymer were deprotected by dissolution of the polymer in trifluoroacetic acid (100 mg/mL) and treating at 55° C. for 8 hours, resulting in a water soluble polymer. $^1$H NMR (300 MHz, D$_2$O, ppm) δ 1.10-1.70, m, 6 H; 2.9-3.6, broad overlapping peak, 3.19, s, 1 H; 3.40, s, 1 H; 7.42-7-71, m, end-group low-resolution peak.

Homopolymerization of 13:

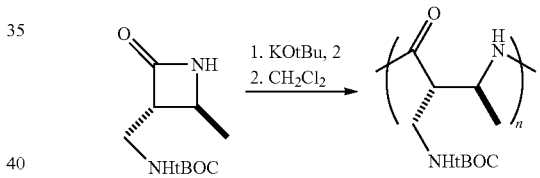

In a 7 mL glass vial, under inert atmosphere, was combined 10 (0.14 mmol, 30 mg), potassium tert-butoxide (KOtBu, 0.01 mmol, 1 mg), and 2 (0.004 mmol, 1 mg). The polymer was isolated as described above for poly(6). The isolated yield was 91% (27 mg). $^1$H NMR (300 MHz, CDCl$_3$, ppm) δ 1.18, broad s, 3 H; 1.43, broad s, 9 H; 2.2, s, 1 H, 2.4-4.4, set of overlapped resonances, 4 H; 7.50, m, end-group low-resolution peak; 7.94, m, end-group low-resolution peak. Deprotected water soluble poly(13) was obtained as described for poly(10). $^1$H NMR (300 MHz, D$_2$O, ppm) δ 1.11, s, 3 H; 2.9, m, 2 H; 3.22, s, 1 H; 4.17, s, 1 H; 7.35-7-62, m, end-group low-resolution peak.

Homopolymerization of 14:

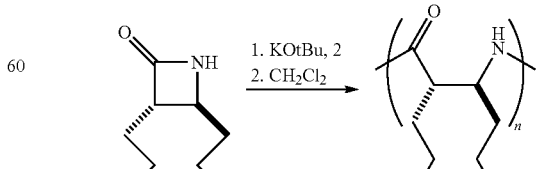

When the general polymerization procedure is applied to 14, the polymerization mixture solidifies within 5 minutes. Polymer is extensively washed with ether resulting in a white powder, insoluble in chloroform, THF, and DMSO.

Homopolymerization of 15:

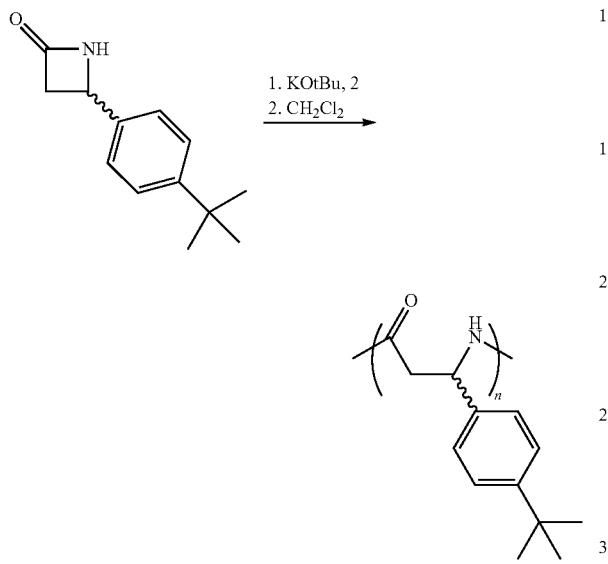

When the general polymerization procedure is applied to 14, the polymerization mixture stays homogeneous. However when polymer is precipitated in pentane the resulting white powder is insoluble in chloroform, THF, and DMSO.

Example 3

Figure 3:
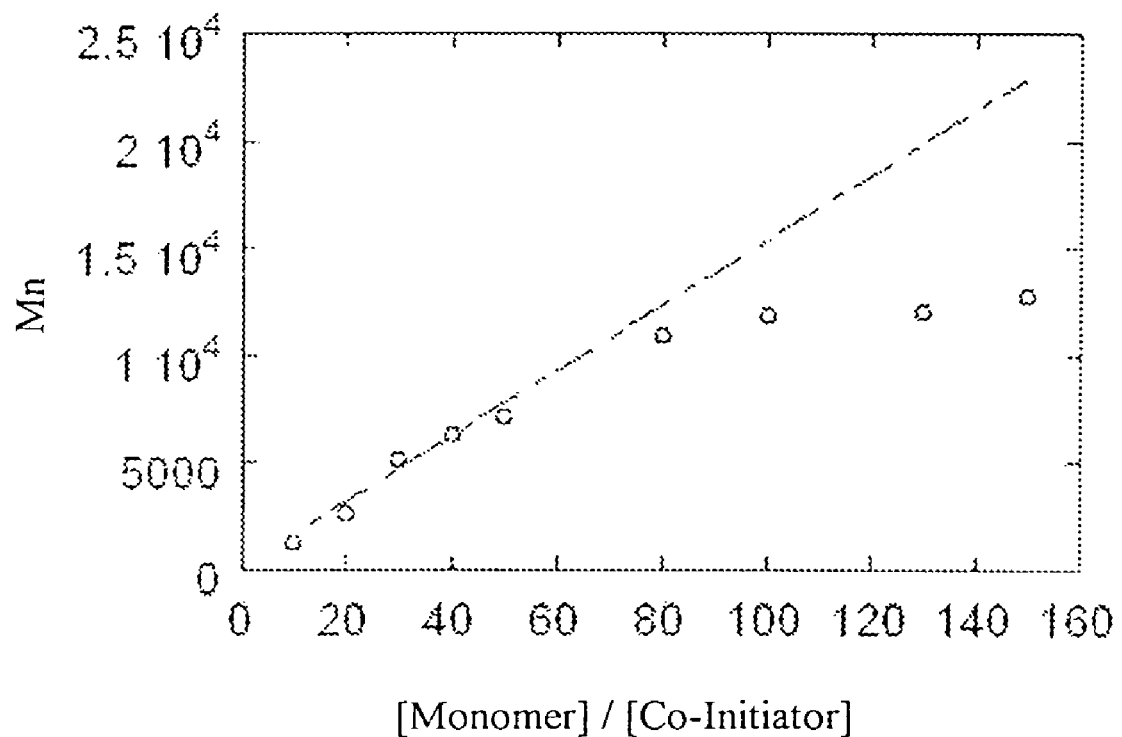
FIG. 3 is graph depicting the linear dependence of product molecular weight ($M_n$) versus the ratio of monomer concentration to co-initiator concentration ([monomer]/[co-initiator]) for the polymerization of compound 6.

Living Polymerization:

(a) Molecular Weight of the Product Polymer as a Function of the Ratio of Monomer-to-Co-Initiator Ratio ([monomer]/[co-initiator]):

A study was conducted to determine if systematically adjusting the ratio of the concentration of monomer reactants to the concentration of the co-initiator ([monomer]/[co-initiator]) would have a corresponding effect on the molecular weight of the resulting polymer product. Compound 6 was used as the monomer for this Example. The results are depicted in FIG. 3, which is a graph depicting [monomer]/[co-initiator] on the X-axis and product molecular weight (Mn) on the Y-axis. As can be seen from FIG. 3, the molecular weight of the polymers obtained versus the [monomer]/[co-initiator] ratio shows a linear, proportional dependence up to about [monomer]/[co-initiator]=80. These results reflect and confirm the living character of the polymerization reaction.

(b) Degenerate Block Co-polymerization:

The living character of polymerization was also confirmed by carrying out degenerate block-copolymerization of monomer 6 as shown in Reaction Scheme 6:

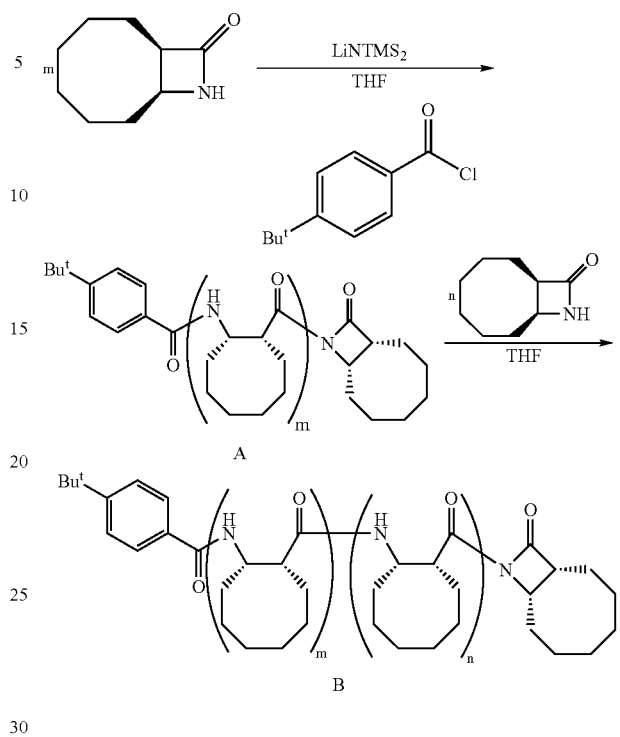

The GPC curves, shown in FIGS. 4 and 5, show the complete consumption of the initial polymer product A (FIG. 4) and the appearance of a degenerate monomodal block-copolymer product B (FIG. 5). Polymerization of compound 6 with MeONa and compound 5 with $LiN(SiMe_3)_2$ were also confirmed to proceed in living fashion. This is significant because it allows for exquisite control of the product using homopolymerization or copolymerization.

Example 4

Random Copolymerizations:

The general polymerization procedure was applied to mixtures of monomers resulting in polymers without any broadening in molecular weight distributions. $^1$H NMR analysis showed the presence of all resonances from individual homopolymers overlapped.

Example 5

Block Copolymerizations:

Block copolymers were prepared by sequential comonomer addition. First a desired homopolymer was prepared according to the general polymerization procedures recited above, and after allowing time for the completion of first block (20 to 120 minutes depending on monomer to initiator ratios) a second monomer was added and second block was formed. Alternatively a homopolymer can be isolated by precipitation, redissolved in a polymerization mixture according to the general polymerization procedure as a replacement for coinitiator 2, and lead to growth of a second block from the chain-end of the first block. Comparisons of molecular weights of first block and diblock showed the expected increase in molecular weight without a significant broadening in molecular weight distributions. In particular, see FIG. 2, which shows two superimposed GPC curves for a homopolymer and a diblock co-polymer fabricated using the homopolymer. The earlier eluting peak in FIG. 2 is the diblock copolymer, and the later eluting peak is the homopolymer.

Example 6

Terminal Functionalization:

Because the polymerization proceeds in a living fashion, the termini of the polymer chains can be functionalized using appropriate co-initiators that also function as a terminal co-monomer reactant. Co-monomers for terminal functionalization can include broad classes of functional groups, including hydrophobic, anionic, cationic and neutral hydrophilic groups, without limitation. An attractive feature of the polymerization method is the ability to control the functional groups located at either end of the polymer. The acylating agent used as the co-initiator (in combination with a strong base) functionalizes one end of the polymer chain and the other end of the chain possesses an imide group that will react with suitable nucleophiles (e.g., primary amines) after the polymerization reaction is complete. By exploiting the fundamental characteristics of the inventive polymerization technique, one can introduce a wide range of functional groups into the polymer, both along the main chain (via side chains incorporated into the monomers) and at each end of the polymer (by choosing an appropriate co-initiator and reaction the terminal imide group after polymerization is complete). These functional groups are expected to play a significant role in the biological activity of the material.

In this Example, 4-chloromethyl benzoyl chloride (C) was used as a co-initiator to yield a polymer having a 4-chloromethyl benzoyl terminus. See Reaction Scheme 7:

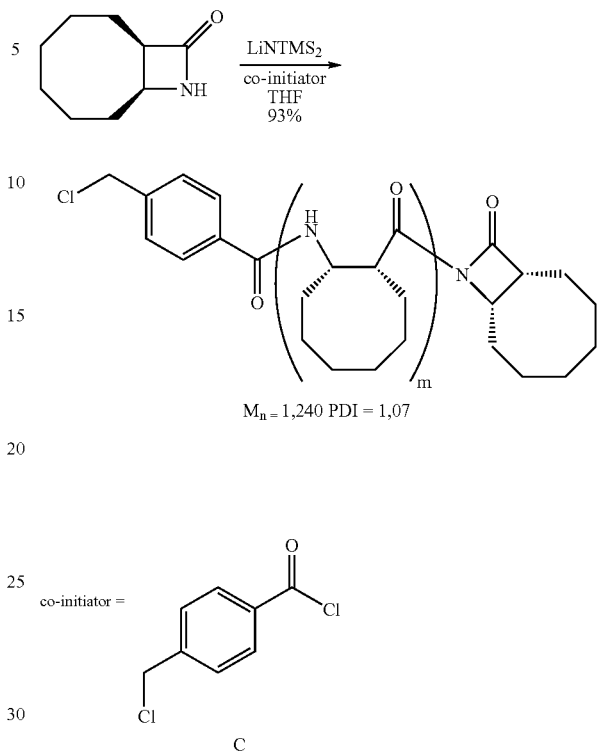

Further chemical modification of the 4-chloromethyl end-group yielded a host of end-group functionalized β-polypeptide polymer derivatives as shown in Reaction Scheme 8:

Reaction Scheme 8
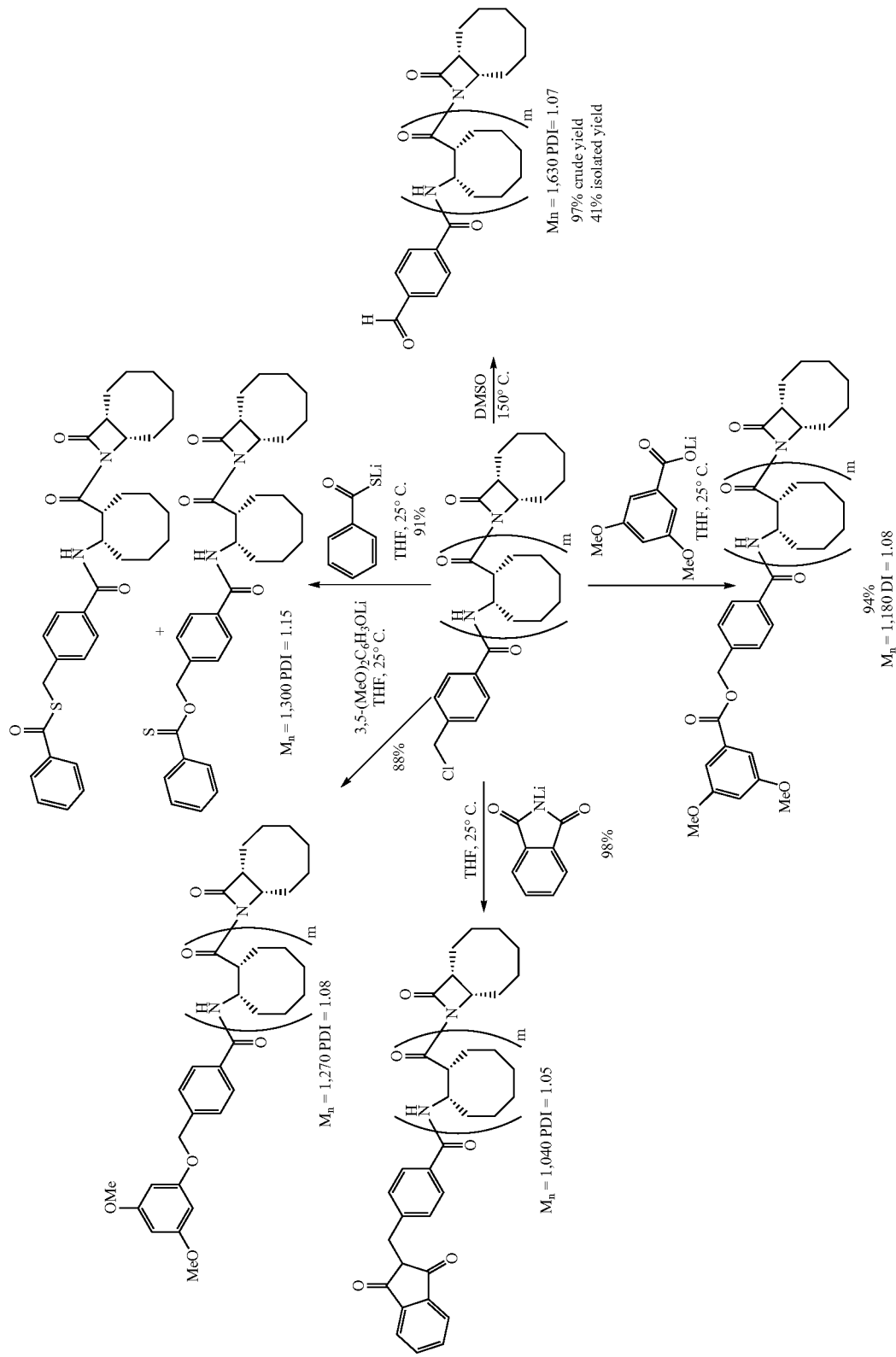

As shown in Reaction Scheme 8, the reactive 4-chloromethyl group can be used to append various functional end groups in high yields, such as aldehyde, esters, thioesters, amines and imides (phthalimide followed by deprotection), and the like.

An α,β-unsaturated carbonyl terminus can be appended to the polymer chain by running the reaction using an appropriate co-initiator, as shown in Reaction Scheme 9:

Reaction Scheme 9

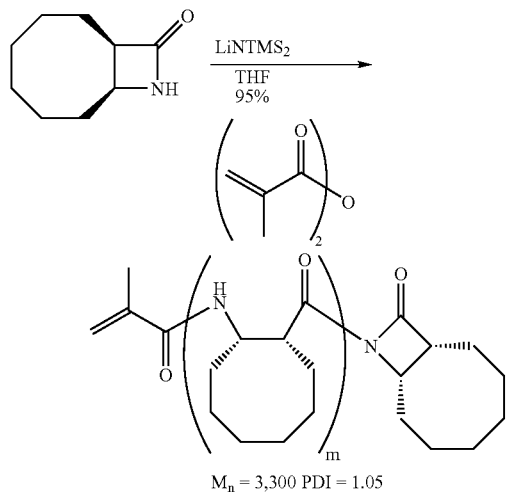

$M_n = 3,300$ PDI $= 1.05$

As in the case of Reaction Scheme 8, the terminal methylene group can function as a reactive site to allow for further modification of the polymer chain.

Example 7

Measurement for Antibacterial Activities of Poly-β-Peptides:

The bacteria strains used in these assays were *Escherichia coli* JM 109, *Bacillus subtilis* BR151, *Staphylococcus aureus* 1206 (methicillin-resistant), and *Enterococcus faecium* A634 (vancomycin-resistant). The antibacterial activity for the poly-b-peptides was determined in sterile 96-well plates (Falcon 3075 microtiter plate) by a microdilution method. A bacterial suspension of approximately $10^6$ CFU/M1 in BHI medium was added in 50 µL aliquots to 50 µL of medium containing the poly-β-peptides in 2-fold serial dilutions for a total volume of 100 µL in each well. The plates were incubated at 37° C. for 6 hours. Growth inhibition was determined by measuring the OD at wavelengths ranging from 595-650 nm. Each MIC is the result of at least two separate trials: each trial is the result of an assay run in duplicate. MIC determinations were reproducible to within a factor of two and are reported as the highest (most conservative) of the determined values.

Example 8

Measurement for Hemolytic Activities of Poly-β-Peptides:

Freshly drawn human red blood cells (hRBC, blood type A) were washed several times with Tris buffer (pH 7.2, 150 mM NaCl) and centrifuged at 2000× rpm until the supernatant was clear. Two-fold dilutions of poly-β-peptides in Tris buffer (pH 7.2, 150 mM NaCl) were added to each well in a sterile 96-well plate (Falcon 3075 microtiter plate), for a total volume of 20 µL in each well. A 1% v/v hRBC suspension (80 µL in Tris buffer) was added to each well. The plate was incubated at 37° C. for 1 hour and then the cells were pelleted by centrifugation at 3500 rpm for 5 minutes. The supernatant (80 µL) was diluted with Millipore water (80 µL), and hemoglobin was detected by measuring the OD at 405 nm. The OD of cells incubated with mellitin at 400 µg/mL defines 100%; the OD of cells incubated in Tris buffer defines 0%.

What is claimed is:

1. A method of making β-polypeptides comprising polymerizing β-lactam-containing monomers in an organic solvent in the presence of a base initiator selected from the group consisting of KOtBu, LiN(TMS)$_2$, KN(TMS)$_2$, NaOEt, Sc(N(TMS)$_2$)$_3$, Al$_2$(N(Me)$_2$)$_6$, Al(N(TMS)$_2$)$_3$, Zn(N(TMS)$_2$)$_2$, Sn(N(TMS)$_2$)$_2$, and CpTi(N(Me)$_2$)$_2$Cl, and a co-initiator which is not a metal-containing molecule, wherein the co-initiator is selected from the group consisting of:

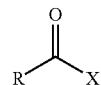

wherein X is a leaving group selected from the group consisting of alkoxide, amidate, carboxylate, halide, imidazolate, lactamate, and thiolate; and R is a base-stable moiety selected from the group consisting of linear, branched, or cyclic alkyl, alkenyl, alkynyl, substituted or unsubstituted aryl, and substituted or unsubstituted arylalkyl;

provided that the co-initiator is not an N-acyl-β-lactam.

2. The method of claim 1, wherein at least one of β-lactam-containing monomers is selected from the group consisting of:

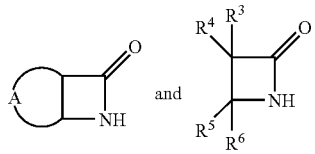

wherein A, together with the carbon atoms to which it is attached is selected from the group consisting of substituted or unsubstituted C$_5$-C$_{12}$ cycloalkyl, C$_5$-C$_{12}$ cycloalkenyl, and five-to twelve-membered heterocyclic; and R$^3$, R$^4$, R$^5$, and R$^6$ are each independently selected from the group consisting of hydrogen, substituted or unsubstituted C$_1$-C$_6$-alkyl, aryl, C$_1$-C$_6$-alklyaryl, amino, protected-amino, amino- C$_1$-C$_6$-alkyl, and protected-amino-C$_1$-C$_6$-alkyl.

3. The method of claim 2, wherein at least one of the β-lactam-containing monomer is selected from the group consisting of:

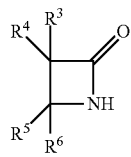

wherein at least one of $R^3$, $R^4$, $R^5$, or $R^6$ is selected from the group consisting of amino, protected amino, amino-$C_1$-$C_6$-alkyl and protected amino-$C_1$-$C_6$-alkyl.

4. The method of claim 1, comprising polymerizing the β-lactam-containing monomers in a solvent selected from the group consisting of chloroform, dichloromethane, dimethylsulfoxide, and tetrahydrofuran.

5. The method of claim 1, comprising polymerizing at least two different β-lactam-containing monomers to yield a co-polymer.

6. The method of claim 1, comprising polymerizing the β-lactam-containing monomers at a temperature ≦ about 50° C.

7. The method of claim 1, comprising polymerizing the β-lactam-containing monomers at a temperature ≦ about 30° C.

8. A method of making β-polypeptides comprising: polymerizing β-lactam-containing monomers in the presence of a base initiator selected from the group consisting of KOtBu, LiN(TMS)$_2$, KN(TMS)$_2$, NaOEt, Sc(N(TMS)$_2$)$_3$Al$_2$(N(Me)$_2$)$_6$, Al(N(TMS)$_2$)$_3$, Zn(N(TMS)$_2$)$_2$, Sn(N(TMS)$_2$)$_2$, and CpTi(N(Me)$_2$)$_2$Cl, and a co-initiator which is not a metal-containing molecule, wherein the β-lactam-containing monomers include a monomer selected from the group consisting of:

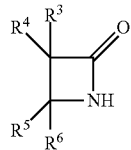

wherein $R^3$, $R^4$, $R^5$, and $R^6$ are each independently selected from the group consisting of hydrogen, substituted or unsubstituted $C_1$-$C_6$-alkyl, aryl, $C_1$-$C_6$-alklyaryl, amino, protected-amino, amino-$C_1$-$C_6$-alkyl, and protected-amino-$C_1$-$C_6$-alkyl; and wherein at least one of $R^3$, $R^4$, $R^5$, or $R^6$ is selected from the group consisting of amino, protected amino, amino-$C_1$-$C_6$-alkyl, and protected-amino-$C_1$-$C_6$-alkyl, wherein the co-initiator is selected from the group consisting of:

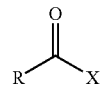

wherein X is a leaving group selected from the group consisting of alkoxide, amidate, carboxylate, halide, imidazolate, lactamate, and thiolate; and R is a base-stable moiety selected from the group consisting of linear, branched, or cyclic alkyl, alkenyl, alkynyl, substituted or unsubstituted aryl, and substituted or unsubstituted arylalkyl, provided that the co-initiator is not an N-acyl-β-lactam.

9. The method of claim 8, comprising polymerizing the β-lactam-containing monomers in a solvent selected from the group consisting of chloroform, dichloromethane, dimethylsulfoxide, and tetrahydrofuran.

10. The method of claim 8, comprising polymerizing at least two different β-lactam-containing monomers to yield a co-polymer.

11. The method of claim 8, comprising polymerizing the β-lactam-containing monomers at a temperature ≦ about 50° C.

12. The method of claim 8, comprising polymerizing the β-lactam-containing monomers at a temperature ≦ about 30° C.

* * * * *